(12) United States Patent
Souda et al.

(10) Patent No.: US 8,877,886 B2
(45) Date of Patent: Nov. 4, 2014

(54) PRODUCTION METHOD OF DEODORIZED POLYOXYALKYLENE-MODIFIED POLYSILOXANE COMPOSITION

(75) Inventors: Tatsuo Souda, Ichihara (JP); Seiki Tamura, Ichihara (JP)

(73) Assignee: Dow Corning Toray Co., Ltd., Chiyoda-Ku, Tokyo (JP)

(*) Notice: Subject to any disclaimer, the term of this patent is extended or adjusted under 35 U.S.C. 154(b) by 134 days.

(21) Appl. No.: 13/513,741

(22) PCT Filed: Dec. 2, 2010

(86) PCT No.: PCT/JP2010/072071
§ 371 (c)(1),
(2), (4) Date: Jun. 4, 2012

(87) PCT Pub. No.: WO2011/068251
PCT Pub. Date: Jun. 9, 2011

(65) Prior Publication Data
US 2012/0245305 A1    Sep. 27, 2012

(30) Foreign Application Priority Data

Dec. 4, 2009 (JP) ................................. 2009-277015

(51) Int. Cl.
| C08G 77/08 | (2006.01) |
| C08G 77/34 | (2006.01) |
| C08G 77/46 | (2006.01) |
| A61K 8/894 | (2006.01) |
| A61Q 19/00 | (2006.01) |
| A61Q 1/02 | (2006.01) |
| A61Q 17/04 | (2006.01) |

(52) U.S. Cl.
CPC ................ *C08G 77/46* (2013.01); *C08G 77/34* (2013.01); *A61Q 1/02* (2013.01); *A61Q 17/04* (2013.01); *A61K 8/894* (2013.01); *A61Q 19/00* (2013.01)
USPC .................... 528/23; 528/31; 528/29; 528/15; 556/445

(58) Field of Classification Search
USPC ................................. 556/445; 528/23, 29, 31
See application file for complete search history.

(56) References Cited

U.S. PATENT DOCUMENTS

| 5,118,764 A |   | 6/1992 | Ichinohe et al. |
| 5,159,096 A | * | 10/1992 | Austin et al. .................. 556/445 |
| 5,225,509 A | * | 7/1993 | Heinrich et al. ................ 528/12 |
| 5,288,831 A | * | 2/1994 | Ichinohe et al. ................ 528/25 |
| 5,986,122 A | * | 11/1999 | Lewis et al. ................... 556/445 |
| 6,162,888 A | * | 12/2000 | Lee et al. ....................... 528/25 |
| 7,709,671 B2 |   | 5/2010 | Nishijima et al. |
| 2003/0158363 A1 |   | 8/2003 | Nakanishi |
| 2004/0253197 A1 | * | 12/2004 | Sakuta ......................... 424/70.12 |
| 2006/0018935 A1 |   | 1/2006 | Nishijima et al. |
| 2007/0212319 A1 | * | 9/2007 | Otterson et al. ............ 424/70.12 |
| 2008/0009600 A1 | * | 1/2008 | Lu et al. ........................... 528/12 |
| 2013/0177516 A1 | * | 7/2013 | Tamura et al. ............. 424/70.12 |

FOREIGN PATENT DOCUMENTS

| JP | 2-302438 | 12/1990 |
| JP | H04-174672 A | 6/1992 |
| JP | H05-004095 A | 1/1993 |
| JP | H07-330907 A | 12/1995 |
| JP | H09-012723 A | 1/1997 |
| JP | H09-165318 A | 6/1997 |
| JP | H09-202829 A | 8/1997 |
| JP | H11-197448 A | 7/1999 |
| JP | 2000-026737 A | 1/2000 |
| JP | 2002-360681 A | 12/2002 |
| JP | 2003-096192 A | 4/2003 |
| JP | 2004-189959 | 7/2004 |
| JP | 2005-120293 | 5/2005 |
| JP | 2005-120293 A | 5/2005 |
| WO | WO 02/055588 A1 | 7/2002 |
| WO | WO 2004046226 A1 | 6/2004 |

OTHER PUBLICATIONS

English language abstract for JP 2-302438 extracted from the espacenet.com database on Jul. 16, 2012, 7 pages.
English language abstract and translation for JP 2004-189959 extracted from the PAJ database on Jul. 16, 2012, 38 pages.
English language abstract and translation for JP 2005-120293 extracted from the PAJ database on Jul. 16, 2012, 158 pages.
English language abstract for WO 2004046226 extracted from the espacenet.com database on Jul. 16, 2012, 43 pages.
International Search Report for Application No. PCT/JP2010/072071 dated Feb. 10, 2011, 3 pages
English language abstract for JP H04-174672 extracted from the espacenet.com database on Dec. 6, 2013, 4 pages.
English language abstract and machine-assisted English translation for JP H05-004095 extracted from the PAJ database on Dec. 4, 2013, 42 pages.
English language abstract and machine-assisted English translation for JP H07-330907 extracted from the PAJ database on Dec. 6, 2013, 27 pages.

(Continued)

*Primary Examiner* — Margaret Moore
(74) *Attorney, Agent, or Firm* — Howard & Howard Attorneys PLLC

(57) ABSTRACT

To provide a method of producing a polyoxyalkylene-modified polysiloxane composition that is free of acid-mediated carbon-oxygen bond and silicon-oxygen bond cleavage, that is substantially deodorized and also does not generate odor with elapsed time, and that is therefore well suited for use in cosmetic applications, e.g., for hair cosmetics, skin cosmetics, and so forth. A production method of this invention is characterized by removing the odor-causing substance from a polyoxyalkylene-modified polysiloxane composition that has been synthesized by a hydrosilylation reaction, by subjecting the polyoxyalkylene-modified polysiloxane composition to a hydrolysis treatment in the presence of an acidic inorganic salt that is a solid at 25° C. and gives a specific pH at 25° C. in aqueous solution; for example, potassium hydrogensulfate.

8 Claims, No Drawings

(56) References Cited

OTHER PUBLICATIONS

English language abstract and machine-assisted English translation for JP H09-012723 extracted from the PAJ database on Dec. 6, 2013, 46 pages.

English language abstract and machine-assisted English translation for JP H09-165318 extracted from the PAJ database on Dec. 6, 2013, 41 pages.

English language abstract and machine-assisted English translation for JP H09-202829 extracted from the PAJ database on Dec. 6, 2013, 43 pages.

English language abstract and machine-assisted English translation for JP H11-197448 extracted from the PAJ database on Dec. 4, 2013, 27 pages.

English language abstract and machine-assisted English translation for JP 2000-026737 extracted from the PAJ database on Dec. 6, 2013, 42 pages.

English language abstract and machine-assisted English translation for JP 2002-360681 extracted from the PAJ database on Dec. 4, 2013, 21 pages.

English language abstract and machine-assisted English translation for JP 2003-096192 extracted from the PAJ database on Dec. 6, 2013, 34 pages.

English language abstract and machine-assisted English translation for JP 2005-120293 extracted extracted from the PAJ database on Dec. 4, 2013, 135 pages.

English language abstract for WO 02/055588 extracted from the espacenet.com database on Dec. 4, 2013, 67 pages.

* cited by examiner

PRODUCTION METHOD OF DEODORIZED POLYOXYALKYLENE-MODIFIED POLYSILOXANE COMPOSITION

RELATED APPLICATIONS

This application claims priority to and all the advantages of International Patent Application No. PCT/JP2010/072071, filed on Dec. 2, 2010, which claims priority to Japanese Patent Application No. JP2009-277015, filed on Dec. 2, 2009.

TECHNICAL FIELD

The present invention relates to a method of producing a deodorized polyoxyalkylene-modified polysiloxane composition and to cosmetic ingredients and cosmetic materials that contain this deodorized polyoxyalkylene-modified polysiloxane composition. The present invention more particularly relates to a method of producing a polyoxyalkylene-modified polysiloxane composition that produces very little odor with elapsed time, to cosmetic ingredients that contain the deodorized composition provided by this production method, and to very low odor cosmetic materials that incorporate the deodorized composition provided by this production method.

BACKGROUND ART

Polyoxyalkylene-modified polysiloxane compositions have heretofore been synthesized by a hydrosilylation reaction between an organohydrogenpolysiloxane bearing the silicon-bonded hydrogen group and a polyoxyalkylene having an allyl ether group in terminal position. However, the polyoxyalkylene-modified polysiloxane compositions obtained in this manner have been prone to generate odor with elapsed time, and it has been quite difficult to achieve a scent-free condition when they are used in cosmetic applications, e.g., for hair cosmetics and skin cosmetics, which has placed limitations on their quantity of incorporation and their applications.

This odor is thought to be due to an internal migration by the terminal double bond in the allyl ether group-containing polyoxyalkylene that occurs during the hydrosilylation reaction and that results in the secondary production of the isomeric propenyl ether group-containing polyoxyalkylene, which then undergoes gradual hydrolysis due to the presence of moisture and trace acid in the system to produce odor-causing propionaldehyde.

In order to address this, a method has been introduced in which hydrolysis is forcibly performed after the hydrosilylation reaction by reacting the propenyl ether with an acidic aqueous solution or an acidic substance in order to produce the odor-causing propionaldehyde, which is subsequently removed (refer to Patent Document 1). A method has also been introduced in which the propenyl ether group-containing polyoxyalkylene is degraded using an acidic substance and a lower alcohol in place of water; an adduct is formed between the propionaldehyde and the lower alcohol; and these are thereafter removed (refer to Patent Document 2). However, in both of these methods only mineral acids such as hydrochloric acid, sulfuric acid, or nitric acid, organic acids such as formic acid or acetic acid, or Lewis acids are provided as examples of the acidic substance. A problem with these acids has been that during the hydrolysis reaction they cleave the carbon-oxygen bond in the polyoxyalkylene moiety as well as the silicon-oxygen bond in the organopolysiloxane moiety. In addition, excess amounts of acid and water or alcohol are required in order to drive the hydrolysis reaction to completion, and these must then be removed by volatilization. A problem here is that this promotes the previously indicated acid-mediated cleavage of the carbon-oxygen bond and silicon-oxygen bond.

In order to solve the problems posed by these acids, a method has been introduced in which the hydrosilylation reaction is followed by treatment in the presence of a solid acid (refer to Patent Document 3). However, contact with the propenyl ether group-containing polyoxyalkylene is not adequate when a solid acid is used, resulting in inadequate hydrolysis and the occurrence of odor generation with elapsed time. In addition, when the amount used has been increased in order to boost the efficiency, problems have arisen such as an impaired workability due to escape during filtration, an impaired workability due to clogging during the filtration process, and a tendency for discoloration to occur. Furthermore, solid acids are also known to function as polycondensation reaction catalysts, and as a result the previously indicated acid-mediated carbon-oxygen bond and silicon-oxygen bond cleavage still similarly occurs. Moreover, solid acids are insoluble in both water and organic solvents, which complicates the ensuing washing step.

[Patent Document 1] JP 02-302438 A (JP 07-091389 B)
[Patent Document 2] JP 2004-189959 A (JP 4,064,223 B)
[Patent Document 3] WO 2004/046226

SUMMARY OF INVENTION

Technical Problems to be Solved

The present invention seeks to solve the problems identified above and has as an object the introduction of a method of producing a polyoxyalkylene-modified polysiloxane composition that is free of acid-mediated carbon-oxygen bond and silicon-oxygen bond cleavage, that is substantially deodorized and also does not generate odor with elapsed time, and that is therefore well suited for use in cosmetic applications, e.g., for hair cosmetics, skin cosmetics, and so forth. Additional objects of the present invention are to provide a cosmetic ingredient that contains a polyoxyalkylene-modified polysiloxane composition and is free of a peculiar or distinctive odor and to provide a very low odor cosmetic material that incorporates a polyoxyalkylene-modified polysiloxane composition.

Solution to Problems

The objects of the present invention are achieved by a production method of a polyoxyalkylene-modified polysiloxane composition wherein this method characteristically comprises:

a step [A] of synthesizing a polyoxyalkylene-modified polysiloxane composition by carrying out a hydrosilylation reaction between
(a) a polyoxyalkylene compound that has a carbon-carbon double bond in molecular chain terminal position and
(b) an organohydrogenpolysiloxane; and
a step [B] of removing an odor-causing substance by treating the polyoxyalkylene-modified polysiloxane composition in the presence of
(c) at least one acidic inorganic salt that characteristically is a solid at 25° C., is soluble in water, and gives a pH at 25° C. of not more than 4 for the aqueous solution prepared by dissolving 50 g in 1 liter of ion-exchanged water. The objects of the present invention are also achieved by a cosmetic ingredient and a cosmetic material that contain the polyoxyalkylene-modified polysiloxane composition provided by this production method.

The objects of the present invention are particularly suitably achieved by the use as component (c) of at least one acidic inorganic salt selected from the group consisting of sodium hydrogensulfate, potassium hydrogensulfate, and ammonium hydrogensulfate. The objects of the present invention are even more suitably achieved by a production method of a polyoxyalkylene-modified polysiloxane composition that characteristically comprises the previously indicated steps [A] and [B] and also a step [C] of carrying out a deodorization treatment by subjecting the polyoxyalkylene-modified polysiloxane composition to a hydrogenation reaction in the presence of a hydrogenation catalyst. The objects of the present invention are likewise achieved by a cosmetic ingredient and a cosmetic material that contain the polyoxyalkylene-modified polysiloxane composition provided by this production method.

That is, the objects indicated above are achieved by

"[1] A production method of a polyoxyalkylene-modified polysiloxane composition comprising:
a step [A] of synthesizing a polyoxyalkylene-modified polysiloxane composition by carrying out a hydrosilylation reaction between
(a) a polyoxyalkylene compound that has a carbon-carbon double bond in molecular chain terminal position and
(b) an organohydrogenpolysiloxane; and
a step [B] of removing an odor-causing substance by treating the polyoxyalkylene-modified polysiloxane composition in the presence of
(c) at least one acidic inorganic salt that characteristically is a solid at 25° C., is soluble in water, and gives a pH at 25° C. of not more than 4 for the aqueous solution prepared by dissolving 50 g in 1 liter of ion-exchanged water.

[2] The production method according to [1], wherein component (c) is at least one acidic inorganic salt comprising a hydrogensulfate ion $HSO_4^-$ and a monovalent cation $M^+$.

[3] The production method according to [1] or [2], wherein component (c) is at least one acidic inorganic salt selected from the group consisting of sodium hydrogensulfate, potassium hydrogensulfate, and ammonium hydrogensulfate.

[4] The production method according to any of [1] to [3] further comprises:
a step [C] of carrying out a deodorization treatment by subjecting the polyoxyalkylene-modified polysiloxane composition to a hydrogenation reaction in the presence of a hydrogenation catalyst.

[5] The production method according to [4], which is characterized in that step [C] is carried out subsequent to step [B].

[5-1] The production method according to [5], which is particularly characterized in that the hydrogenation catalyst in step [C] is a Raney nickel catalyst.

[6] The production method according to [4], which is characterized in that step [B] is carried out subsequent to step [C].

[6-1] The production method according to [6], which is particularly characterized in that the hydrogenation catalyst in step [C] is a Raney nickel catalyst.

[7] The production method according to any of [1] to [6], which is characterized in that component (a) in step [A] is a straight-chain polyoxyalkylene compound given by the following structural formula (1)

$$CH_2=CH-C_pH_{2p}O-(C_2H_4O)_{p1}(C_3H_6O)_{p2}R \qquad (1)$$

wherein p is a number in the range from 1 to 10, p1 and p2 are numbers in the range from 0 to 30, (p1+p2) is a number in the range from 4 to 50, and R is the hydrogen atom or a $C_{1-10}$ alkyl group, and
component (b) in step [A] is an organohydrogenpolysiloxane given by the following structural formula (2)

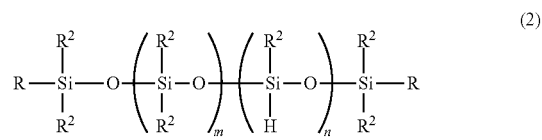

wherein $R^2$ is a substituted or unsubstituted monovalent hydrocarbyl group, R is the hydrogen atom or a group selected from $R^2$, m is a number in the range from 0 to 1000, and n is a number in the range from 0 to 200, wherein when n=0, at least one of R is the hydrogen atom.

[7-1] The production method according to [7], wherein $R^2$ in structural formula (2) is a $C_{1-30}$ alkyl group and at least 50 mol % of the total $R^2$ is the methyl group.

[8] The production method according to any of [1] to [7] further has, as a step preceding step [B] or a step following step [B],
a stripping step of distillatively removing a low-boiling fraction from the polyoxyalkylene-modified polysiloxane composition under reduced pressure while in contact with nitrogen gas.

[9] A cosmetic ingredient comprising a polyoxyalkylene-modified polysiloxane composition obtained by the production method according to any of [1] to [8].

[10] A cosmetic material comprising a polyoxyalkylene-modified polysiloxane composition obtained by the production method according to any of [1] to [8]."

Advantageous Effects of Invention

The method of the present invention for producing a polyoxyalkylene-modified polysiloxane composition provides a method of producing a polyoxyalkylene-modified polysiloxane composition that is free of acid-mediated carbon-oxygen bond and silicon-oxygen bond cleavage, that is substantially deodorized and also does not generate odor with elapsed time, and that is therefore well suited for use in cosmetic applications, e.g., for hair cosmetics, skin cosmetics, and so forth. The present invention additionally provides a cosmetic ingredient that contains a polyoxyalkylene-modified polysiloxane composition and is free of a peculiar or distinctive odor. The present invention additionally provides a very low odor cosmetic material that incorporates a polyoxyalkylene-modified polysiloxane composition.

BEST MODE FOR CARRYING OUT THE INVENTION

The method according to the present invention for producing a polyoxyalkylene-modified polysiloxane composition, the cosmetic ingredient comprising this composition, and the cosmetic material that incorporates this composition are described in detail herebelow.

The method according to the present invention is a production method of a polyoxyalkylene-modified polysiloxane composition that characteristically comprises
a step [A] of synthesizing a polyoxyalkylene-modified polysiloxane composition by carrying out a hydrosilylation reaction between (a) a polyoxyalkylene compound that has a carbon-carbon double bond in molecular chain terminal position and
(b) an organohydrogenpolysiloxane; and
a step [B] of removing an odor-causing substance by treating the polyoxyalkylene-modified polysiloxane composition in the presence of
(c) at least one acidic inorganic salt that characteristically is a solid at 25° C., is soluble in water, and gives a pH at 25° C. of not more than 4 for the aqueous solution prepared by dissolving 50 g in 1 liter of ion-exchanged water.

<Step [A]>

Step [A] is a step of synthesizing a crude polyoxyalkylene-modified polysiloxane composition product and is performed by carrying out a hydrosilylation reaction between (a) a polyoxyalkylene compound that has a carbon-carbon double bond in molecular chain terminal position and (b) an organohydrogenpolysiloxane.

Component (a) is a polyoxyalkylene compound that has a carbon-carbon double bond in molecular chain terminal position, and it provides the polyoxyalkylene-modified polysiloxane composition according to the present invention, which also possesses the properties provided by the polysiloxane main chain, with the hydrophilicity that originates with the polyoxyalkylene bond. Component (a) is introduced into component (b) by the hydrosilylation reaction.

The polyoxyalkylene compound having a terminal double bond can be exemplified by compounds with the general formula $R^3O(R^4O)_aR^3$ wherein $R^3$ is the hydrogen atom or a monovalent hydrocarbyl group and at least one $R^3$ is an alkenyl group having a terminal double bond, e.g., vinyl, hexenyl, and so forth, and preferably one $R^3$ is a $C_{2-12}$ alkenyl group having a terminal double bond. The monovalent hydrocarbyl group other than the preceding can be exemplified by saturated aliphatic hydrocarbyl groups such as $C_{1-12}$ alkyl; saturated alicyclic hydrocarbyl groups such as cyclopentyl and cyclohexyl; aromatic hydrocarbyl groups such as phenyl, tolyl, and naphthyl; and/or a group as generated by replacing a portion of the carbon-bonded hydrogen in the preceding groups with a halogen atom or an organic group that contains the epoxy group, carboxyl group, or methacryl group. One $R^3$ is preferably the hydrogen atom or a $C_{1-10}$ alkyl group. $R^4$ is a substituted or unsubstituted divalent hydrocarbyl group, for example, ethylene, propylene, butylene, pentylene, phenylene, and alkyl-substituted phenylene. a is 0 or a positive integer and is preferably from 1 to 300 and more preferably is from 1 to 100. A straight-chain polyoxyalkylene compound given by the following structural formula (1)

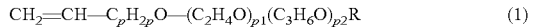

$$CH_2=CH-C_pH_{2p}O-(C_2H_4O)_{p1}(C_3H_6O)_{p2}R \quad (1)$$

and having a polyoxyalkylene unit comprising the oxyethylene group or oxypropylene group is particularly suitable. With reference to structural formula (1), p is a number in the range from 1 to 10 and is particularly preferably a number in the range from 1 to 4. p1 and p2 are numbers in the range from 0 to 30 and preferably at least p1 or p2 is a number in the range from 4 to 20. In addition, (p1+p2) is a number in the range from 4 to 50 and particularly preferably is a number in the range from 8 to 40. Under actual conditions, the values of p1 and p2 for component (a) are average values for the degrees of polymerization of the respective oxyalkylene units, and, since the degree of polymerization of each oxyalkylene unit then has a certain width (distribution), component (a) may be a mixture comprising a plurality of polyoxyalkylene compounds that have different values of p1 and p2. The group R is the hydrogen atom or a $C_{1-10}$ alkyl group and is particularly preferably the hydrogen atom or a methyl group.

The component (a) polyoxyalkylene compound can be exemplified by the compounds given below. A single one of these polyoxyalkylene compounds may be used or a combination of two or more may be used.

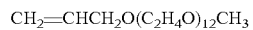
$CH_2=CHCH_2O(C_2H_4O)_{12}CH_3$

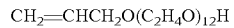
$CH_2=CHCH_2O(C_2H_4O)_{12}H$

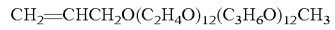
$CH_2=CHCH_2O(C_2H_4O)_{12}(C_3H_6O)_{12}CH_3$

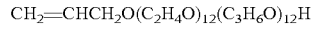
$CH_2=CHCH_2O(C_2H_4O)_{12}(C_3H_6O)_{12}H$

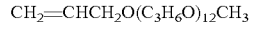
$CH_2=CHCH_2O(C_3H_6O)_{12}CH_3$

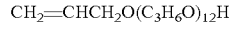
$CH_2=CHCH_2O(C_3H_6O)_{12}H$

Component (b) is an organohydrogenpolysiloxane, and the organohydrogenpolysiloxane used in the present invention preferably contains at least one silicon-bonded hydrogen atom in each molecule. The constituent siloxane units therein are represented by the general formula $R^1_aSiO_{(4-a)/2}$. $R^1$ in this formula is the hydrogen atom or a substituted or unsubstituted monovalent hydrocarbyl group. This monovalent hydrocarbyl group can be specifically exemplified by saturated aliphatic hydrocarbyl groups as typified by $C_{1-30}$ alkyl, e.g., methyl, ethyl, propyl, butyl, pentyl, hexyl, heptyl, octyl, decyl, and dodecyl; saturated alicyclic hydrocarbyl groups such as cyclopentyl and cyclohexyl; aromatic hydrocarbyl groups such as phenyl, tolyl, naphthyl, and alkylbenzyl; and/or a group as generated by replacing a portion of the carbon-bonded hydrogen in the preceding groups with a halogen atom or an organic group that contains the epoxy group, carboxyl group, or methacryl group. The monovalent hydrocarbyl groups may be the same as each other or may differ from one another.

$R^1$ is preferably an alkyl group wherein methyl is more preferred. However, at least one $R^1$ in the siloxane units constituting the component (b) organohydrogenpolysiloxane is the hydrogen atom. a is 0<a≤3 on average. There is no limitation on the molecular structure of this organohydrogenpolysiloxane, which can be exemplified by straight chain, partially branched straight chain, branched chain, cyclic, and dendritic wherein straight chain is preferred. The degree of polymerization of this organohydrogenpolysiloxane is not particularly limited, and a species in the range from low molecular weight to high molecular weight can be used. In specific terms, the number-average molecular weight is preferably in the range from 100 to 1,000,000 and more preferably is in the range from 300 to 500,000.

The organohydrogenpolysiloxane under consideration can be exemplified by the organohydrogenpolysiloxanes given by the following structural formulas. These organohydrogenpolysiloxanes show the structures of straight-chain organohydrogenpolysiloxanes that have silicon-bonded hydrogen (i) only in side chain position, (ii) at one molecular chain terminal and in side chain position, and (iii) at both molecular chain terminals and in side chain position.

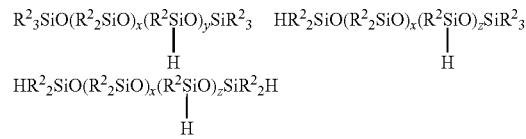

In the preceding formulas, $R^2$ is a substituted or unsubstituted monovalent hydrocarbyl group and can be specifically exemplified by the same groups as provided above as examples of $R^1$. x is 0 or a positive integer; y is a positive integer; and z is 0 or a positive integer.

The straight-chain polysiloxane given by the following structural formula (2) is an example of a straight-chain organohydrogenpolysiloxane that is particularly suitably used in the present invention. A single such organohydrogenpolysiloxane may be used or a combination of two or more may be used.

Structural Formula (2):

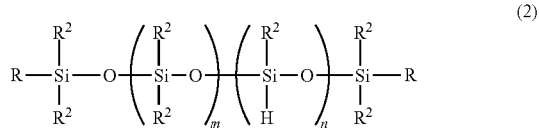

$R^2$ in this formula is a substituted or unsubstituted monovalent hydrocarbyl group and can be exemplified by the same groups as provided above as examples of $R^1$, while in particular $R^2$ is preferably a $C_{1-30}$ alkyl group and at least 50 mol % of the total $R^2$ is particularly preferably the methyl group. In addition, with the goal of improving the compatibility with non-silicone cosmetic ingredients, medium-chain and long-chain $C_{8-30}$ alkyl is preferably selected for the non-methyl $R^2$.

The group R in the preceding formula is the hydrogen atom or a group selected from $R^2$ and particularly preferably is the hydrogen atom or methyl group. m is a number in the range from 0 to 2000 and preferably is a number in the range from 0 to 1000 and more preferably is a number in the range from 0 to 300. n is a number in the range from 0 to 500 and preferably is a number in the range from 0 to 200 and more preferably is a number in the range from 0 to 50. When n=0, at least one R is the hydrogen atom. In addition, when at least one R is a monovalent hydrocarbyl group $R^2$, n is then particularly preferably a number in the range from 1 to 40.

The hydrosilylation reaction for synthesis of the polyoxyalkylene-modified polysiloxane composition can be carried out according to a known method in the presence of a solvent or in the absence of a solvent. This reaction solvent can be exemplified by alcohol solvents such as ethanol, isopropyl alcohol, and so forth; aromatic hydrocarbon solvents such as toluene, xylene, and so forth; ether solvents such as dioxane, THF, and so forth; aliphatic hydrocarbon solvents such as n-hexane, cyclohexane, n-heptane, cycloheptane, methylcyclohexane, and so forth; and chlorinated hydrocarbon-type organic solvents such as carbon tetrachloride and so forth.

The hydrosilylation reaction may be carried out in the absence of a catalyst, but is preferably carried out in the presence of a catalyst because the reaction runs rapidly at low temperatures in the presence of a catalyst. This catalyst can be a compound of, for example, platinum, ruthenium, rhodium, palladium, osmium, iridium, and so forth, wherein platinum compounds are particularly effective due to their high catalytic activity. The platinum compounds can be exemplified by chloroplatinic acid; metallic platinum; metallic platinum supported on a carrier such as alumina, silica, and carbon black; and platinum complexes such as platinum-vinylsiloxane complexes, platinum-phosphine complexes, platinum-phosphite complexes, and platinum-alcohol catalysts. When a platinum catalyst is employed, the quantity of catalyst use is approximately 0.0001 to 0.1 mass % as platinum metal and preferably is in the range from 0.0005 to 0.05 mass % as platinum metal, but is not limited to these values.

The hydrosilylation reaction temperature is generally 50 to 150° C., and the reaction time is generally from 10 minutes to 24 hours and preferably is from 1 to 10 hours.

The ratio [number of moles of carbon-carbon double bonds in component (a)/number of moles of silicon-bonded hydrogen atoms in component (b)] in the hydrosilylation reaction can be, for example, in the range from 1.0 to 2.0. That is, component (a) is preferably used in excess in the synthesis of the polyoxyalkylene-modified polysiloxane composition according to the present invention. More specifically, the indicated ratio between components (a) and (b) is preferably in the range from 1.05 to 1.75 and more preferably is in the range from 1.10 to 1.55. The resulting polyoxyalkylene-modified polysiloxane composition is then a mixture of unreacted component (a) and the polyoxyalkylene-modified polysiloxane, but is obtained as a uniform composition because these components exhibit an excellent compatibility. In addition, after the below-described step [B] and optional step [C], it can be used as a uniform composition as a cosmetic ingredient and can be incorporated as a uniform composition into cosmetic materials.

When, on the other hand, the previously indicated ratio is less than 1.0, unreacted component (b) then remains in the polyoxyalkylene-modified polysiloxane composition according to the present invention. When such a polyoxyalkylene-modified polysiloxane composition is employed as a cosmetic ingredient, the unreacted component (b) can react with other cosmetic ingredients to cause the production of hydrogen gas, which can have undesirable effects such as, for example, a deterioration in the cosmetic material after incorporation, creation of a fire risk, container swelling, and so forth. Thus, in order to bring about the complete reaction of the organohydrogenpolysiloxane, the previously indicated ratio preferably exceeds 1.0, i.e., component (a), which is inserted as the polyoxyalkylene group, is preferably reacted in an excess amount greater than 1 equivalent.

As an example, when the previously indicated hydrosilylation reaction in step [A] is performed using (a) a straight-chain polyoxyalkylene compound with structural formula (1) and (b) a straight-chain organohydrogenpolysiloxane with structural formula (2) with the number of moles of component (a) being an amount in excess to the silicon-bonded hydrogen in component (b), a polyoxyalkylene-modified polysiloxane with the structural formula given below is synthesized and the polyoxyalkylene-modified polysiloxane composition according to the present invention is obtained as a crude product that contains the indicated polyoxyalkylene-modified polysiloxane and unreacted component (a).

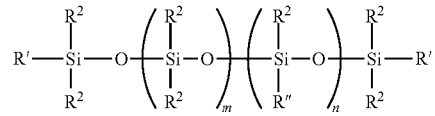

In the preceding formula, $R^2$ is the same group as defined above and R" is a polyoxyalkylene group given by —$C_2H_4$—$C_pH_{2p}O$—$(C_2H_4O)_{p1}(C_3H_6O)_{p2}R$ wherein the ranges for the values of p, p1, and p2 are the same as defined above and R is the same group as defined above. R' is a monovalent hydrocarbyl group $R^2$ or is a group R". m and n are the same as defined above for structural formula (2). When n=0, at least one R' is a group R". In addition, when at least one R is a monovalent hydrocarbyl group $R^2$, n is then particularly preferably a number in the range from 1 to 40.

<Step [B]>

Step [B] is the step that characterizes the method according to the present invention for producing a polyoxyalkylene-modified polysiloxane composition. Step [B], through its execution of a hydrolysis treatment on this composition using a special acidic inorganic salt, is the essential step for bringing about the substantial deodorization of this composition and for almost completely inhibiting odor generation with elapsed time, while avoiding cleavage of the silicon-oxygen bond making up the polysiloxane main chain and the carbon-oxygen bond present in the side chain moiety.

In specific terms, this step [B] is a step in which odor-causing substances are removed by hydrolysis from the crude polyoxyalkylene-modified polysiloxane composition product, and is characterized by performing a treatment in the presence of (c) at least one acidic inorganic salt that characteristically is a solid at 25° C., is soluble in water, and gives a pH at 25° C. of not more than 4 for the aqueous solution prepared by dissolving 50 g in 1 liter of ion-exchanged water. In the present invention, this pH value is the pH value measured using a glass electrode-equipped pH meter on the aqueous sample solution at room temperature (25° C.); a Model HM-10P from the TOA-DENPAKOGYO Corporation was specifically used for pH measurement in the present application.

The component (c) inorganic salt must be a solid at 25° C. and must be water soluble and must provide a pH of not more than 4 and more suitably preferably not more than 3.5 and particularly preferably not more than 2.0 for the aqueous solution prepared by dissolving 50 g in one liter of ion-exchanged water. The execution of the hydrolysis treatment on the composition under consideration using this water-soluble acidic inorganic salt makes possible the substantial deodorization of this composition and an almost complete suppression of odor with elapsed time and does so without causing cleavage of the carbon-oxygen bond or silicon-oxygen bond.

The component (c) acidic inorganic salt can be, for example, an acidic inorganic salt as provided by the neutralization with a base of at least one of the hydrogen atoms in an at least dibasic inorganic acid. The at least dibasic inorganic acid can be exemplified by sulfuric acid, sulfurous acid, and so forth. The base can be exemplified by alkali metals, ammonia, and so forth.

More specifically, component (c) is suitably at least one acidic inorganic salt comprising the bisulfate ion $HSO_4^-$ or the bisulfite ion $HSO_3^-$ and a monovalent cation $M^+$, wherein the monovalent cation $M^+$ can be exemplified by alkali metal ions and the ammonium ion. At least one monovalent cation selected from the group consisting of the sodium ion, potassium ion, and ammonium ion is particularly preferred. A single one of these acidic inorganic salts may be used or a combination of two or more may be used. These acidic inorganic salts are solids at room temperature (25° C.) and can therefore be easily removed by a post-treatment filtration. Because they are water-soluble, they can also be easily washed out with water in a post-production washing step.

On the other hand, a satisfactory reduction in the odor of the post-hydrolysis composition cannot be achieved when the hydrolysis treatment is performed using, for example, an acetate salt or a phosphate salt, which do not satisfy the conditions given for component (c). Moreover, while performing the hydrolysis treatment with a strong acid such as hydrochloric acid or with a known solid acid such as zirconia sulfate can realize a certain odor reduction, this can also result in cleavage of the carbon-oxygen bond or silicon-oxygen bond in the post-hydrolysis composition.

The component (c) acidic inorganic salt can be specifically exemplified by lithium bisulfate, sodium bisulfate, potassium bisulfate, rubidium bisulfate, cesium bisulfate, ammonium bisulfate, and sodium bisulfite and by their hydrates. The following table shows the pH of the aqueous solution prepared by dissolving 50 g of one of these acidic inorganic salts in one liter of ion-exchanged water. The use of at least one acidic inorganic salt selected from the group consisting of sodium bisulfate, potassium bisulfate, and ammonium bisulfate, these being water-soluble acidic inorganic salts that provide a pH of 2.0 or less, is most preferred from the standpoint of the odor-reducing technical effect.

TABLE 1

| acidic inorganic salt | pH (50 g/L) |
|---|---|
| sodium bisulfate | ≤1.5 |
| potassium bisulfate | ≤2.0 |
| ammonium bisulfate | ≤1.5 |
| sodium bisulfite | 3.5 |

This treatment in the presence of an acidic inorganic salt, which is a characteristic feature of the present invention, denotes, for example, (1) a decomposition treatment in which the acidic inorganic salt is added with stirring to the polyoxyalkylene-modified polysiloxane composition reaction system, for example, a reactor such as a flask, provided by the hydrosilylation reaction-mediated synthesis, or (2) an hydrolysis treatment in which the acidic inorganic salt+water or the acidic inorganic salt+water+an organic solvent are added with stirring.

In a particularly preferred embodiment, the hydrolysis treatment is preferably carried out after step [A] by adding the acidic inorganic salt+water to the reaction system containing the crude polyoxyalkylene-modified polysiloxane composition according to the present invention and stirring using mechanical force. The temperature and treatment time for the hydrolysis treatment may be freely selected, but the hydrolysis treatment is preferably carried out at a temperature of 0 to 200° C. and more preferably 50 to 100° C. for a reaction time of about 0.1 to 24 hours and more preferably about 0.5 to 10 hours. The quantity of use of the acidic inorganic salt can be selected as appropriate in conformity with the treatment apparatus and the treatment time, but is preferably in the range from 1 to 500 ppm and more preferably is in the range from 5 to 200 ppm, in each case with reference to the polyoxyalkylene-modified polysiloxane composition.

The production method of the present invention preferably includes a stripping step in which a low-boiling fraction of odor-causing substances such as propionaldehyde and so forth is removed. In addition, by re-performing the acidic inorganic salt treatment after stripping, more of the propenyl ether group-containing polyoxyalkylene can be hydrolyzed and the odor-causing propionaldehyde and so forth can be removed. When this is done, the acidic inorganic salt remains present and for this reason a supplemental addition of fresh acidic inorganic salt need not be made, while the addition of only water will be advantageous. Thus, step [B] and the stripping step may be carried out two or more times with the goal of raising the degree of deodorization.

The "low-boiling component" that is distilled out by the stripping step contains, inter alia, odor-causing propionaldehyde as well as the reaction solvent used in the hydrosilylation reaction of step [A] or in the hydrogenation reaction of step [C], vide infra.

The stripping step, i.e., the distillative removal of the low-boiling component, may be executed, as a step preceding step

[B], on the crude polyoxyalkylene-modified polysiloxane composition product or may be executed, as a step following step [B], on the polyoxyalkylene-modified polysiloxane composition or on the composition provided by the hydrogenation of the polyoxyalkylene-modified polysiloxane composition. The stripping step may also be executed as both a step preceding step [B] and a step following step [B] and is preferably performed following step [B] with the goal of removing the odor-causing propionaldehyde produced by the hydrolysis reaction.

As the method of removal, stripping at ambient pressure or reduced pressure is preferred and its execution at not more than 120° C. is preferred. In order to carry out stripping efficiently, it is preferably carried out under reduced pressure or is preferably carried out while introducing an inert gas, for example, nitrogen. In a specific example of the process for distilling out the low-boiling component, the crude polyoxyalkylene-modified polysiloxane composition product containing the low-boiling component, or the hydrogenate of this crude polyoxyalkylene-modified polysiloxane composition product, is introduced into a flask equipped with a reflux condenser, nitrogen inlet port, and so forth; the interior is evacuated and heated while nitrogen is introduced; and the light substances are distilled out by maintaining a certain pressure and temperature. A pressure of 0.1 to 10.0 kPa, a temperature of 50 to 170° C., and a treatment time of 10 minutes to 24 hours are generally used here.

The polyoxyalkylene-modified polysiloxane composition of the present invention can be subjected to a hydrogenation treatment, designated as <step [C]>, as a step preceding or subsequent to the treatment in the presence of an acidic inorganic salt in accordance with step [B]. The hydrogenation-based deodorization treatment may be carried out as a hydrogenation treatment after the treatment in the presence of the acidic inorganic salt according to step [B], or the treatment in the presence of the acidic inorganic salt according to step [B] may be carried out after execution of the hydrogenation treatment.

<Step [C]>

Step [C] is a step in which a hydrogenation-based deodorization treatment is carried out on the polyoxyalkylene-modified polysiloxane composition after step [A] or after step [B]. The hydrogenation reaction encompasses techniques that employ hydrogen and techniques that employ a metal hydride, and may be a homogeneous reaction or a heterogeneous reaction. A single one of these techniques may be carried out or a combination of these techniques may be implemented. However, considering that it is advantageous for the catalyst used to not remain in the product, a heterogeneously catalyzed hydrogenation reaction using a solid catalyst is most preferred.

A noble metal catalyst, e.g., a platinum catalyst, palladium catalyst, and so forth or a nickel catalyst can generally be used as the solid hydrogenation catalyst under consideration. More specifically, for example, a single catalyst of, e.g., nickel, palladium, platinum, rhodium, cobalt, and so forth, can be used or a catalyst that combines a plurality of metals, e.g., platinum-palladium, nickel-copper-chromium, nickel-copper-zinc, nickel-tungsten, and nickel-molybdenum, can be used. Active carbon, silica, silica-alumina, alumina, and zeolite are examples of the optionally employed catalyst support. For noble metal catalyst systems, the amount of supported metal is 0.1 to 5 mass % and preferably 0.2 to 3 mass %, while for nickel catalyst systems the amount of supported metal is 20 to 70 mass % and preferably 40 to 60 mass %. In addition, the platinum catalyst used in the synthesis step, i.e., in the hydrosilylation reaction, can also be used as such. A single one of these hydrogenation catalysts can be used or a combination of two or more can be used.

Nickel catalysts are suitable hydrogenation catalysts for step [C] in the present invention, wherein nickel/diatomaceous earth and Raney nickel catalysts are preferred. In particular, the use of a Raney nickel catalyst is most preferred from the standpoint of promoting the deodorization brought about by hydrogenation. While the use of a Raney nickel catalyst is economically superior to the use of noble metal catalysts, Raney nickel catalysts are generally developed with a base and then used, and because of this the pH of the reaction solution must in particular be carefully monitored. In addition, because the reaction system becomes weakly alkaline, Raney nickel catalysts offer the advantage of being suitable for use in the production method of the present invention in particular from the standpoint that a hydrolysis reaction brought about by an acidic aqueous solution is effective for deodorization.

The hydrogenation reaction can be performed at ambient pressure or with the application of pressure and is generally desirably performed at from 1 to 100 MPa at from 50 to 200° C. In practical terms it is performed under a hydrogen overpressure, e.g., a hydrogen pressure of 0.1 to 20 MPa or approximately 1 to 200 kg/cm$^2$. The reaction temperature is preferably 50 to 170° C. from the standpoint of shortening the reaction time. The hydrogenation reaction may also be run in the presence of a solvent, and a suitable selection from the previously described alcohol solvents, aromatic hydrocarbon solvents, ether solvents, aliphatic hydrocarbon solvents, and chlorinated hydrocarbon-type organic solvents can be used.

The hydrogenation reaction may be run using a batch or continuous regime. The reaction time in the case of the batch regime, while varying as a function of the amount of catalyst and the reaction temperature, is in the range from approximately 3 to 12 hours. The hydrogenation reaction endpoint in the case of the batch regime can be taken to be the time point at which the reaction has been continued for an additional 1 to 2 hours after the point at which the decline in the hydrogen pressure becomes almost undetectable during careful monitoring with a pressure gauge. When the hydrogen pressure declines during the course of the reaction, maintenance of an elevated hydrogen pressure by re-introducing hydrogen is preferred from the standpoint of shortening the reaction time.

After the completion of the hydrogenation reaction, the hydrogenate of the polyoxyalkylene-modified polysiloxane composition can be obtained by separating and removing the hydrogenation reaction catalyst, i.e., the hydrosilylation reaction catalyst when it is present in the reaction system, under a nitrogen overpressure using filter paper, diatomaceous earth, or active carbon and then distilling off the solvent.

The polyoxyalkylene-modified polysiloxane composition provided by the production method according to the present invention is gradually oxidized and altered by atmospheric oxygen. In order to stop this, the oxidation stability can be raised by the addition of an oxidation inhibitor, e.g., a phenol type, hydroquinone type, benzoquinone type, aromatic amine type, vitamin type, and so forth, and this addition is preferred. For example, BHT (2,6-di-tert-butyl-p-cresol), vitamin C, vitamin E, and so forth can be used as this oxidation inhibitor. When an oxidation inhibitor is used, its quantity of addition is in the range from 10 to 1000 mass-ppm and preferably 50 to 500 mass-ppm, in each case with reference to the polyoxyalkylene-modified polysiloxane composition.

<The Deodorized Polyoxyalkylene-Modified Polysiloxane Composition>

The polyoxyalkylene-modified polysiloxane composition according to the present invention is obtained by the production method of the present invention comprising the previously described step [A] and step [B] and the optionally executed step [C] and stripping step. The polyoxyalkylene-modified polysiloxane composition does not generate odor with elapsed time and hence can be advantageously used even in those fields in which achieving a scent-free condition has been quite problematic, centering on skin and hair cosmetics, cleansers, and various treatment agents for, e.g., fibers.

In specific terms, the polyoxyalkylene-modified polysiloxane composition provided by the production method of the present invention, due to the execution of the deodorization treatment comprising the step [B] hydrolysis in the presence of a special acidic inorganic salt and the optional step [C] hydrogenation reaction, is substantially odorless and does not invoke the perception of a characteristic or peculiar odor, i.e., an unpleasant smell, and provides an almost complete suppression of odor generation with elapsed time. This composition is also homogeneous as a whole because cleavage of the silicon-oxygen bond constituting the polysiloxane main chain and cleavage of the carbon-oxygen bond in the side chain moiety do not occur in step [B]. As a consequence, the polyoxyalkylene-modified polysiloxane composition provided by the production method of the present invention is well suited for use in cosmetic applications and is well suited for incorporation as an ingredient in various cosmetic materials. In particular, it is preferably used in the range from approximately 0.1 to 40 mass % of the cosmetic material as a whole or cosmetic product as a whole.

<The Cosmetic Material>

The cosmetic material of the present invention characteristically contains the deodorized polyoxyalkylene-modified polysiloxane composition provided by the production method of the present invention. This cosmetic material can be exemplified by cosmetic materials that contain a known polyoxyalkylene-modified polysiloxane, also known as a polyether-modified silicone, and by applications and combinations with the same components as the cosmetic ingredient components described for cosmetic materials that contain a known polyoxyalkylene-modified polysiloxane.

Skin cosmetics and hair cosmetics that contain the deodorized polyoxyalkylene-modified polysiloxane composition provided by the production method of the present invention are more specific examples.

The skin cosmetics according to the present invention are skin cosmetics that contain the deodorized polyoxyalkylene-modified polysiloxane composition provided by the production method of the present invention. The form of the skin cosmetic is not particularly limited and can be exemplified by solutions, creams, solids, semisolids, gels, and emulsion compositions in the form of water-in-oil emulsion compositions and oil-in-water emulsion compositions. The skin cosmetic according to the present invention can be specifically exemplified by basic cosmetics such as facial lotions, milky lotions, creams, sunscreen lotions, sunscreen creams, hand creams, cleansing cosmetics, massage products, cleansers, antiperspirants, deodorants, and so forth, and by make-up cosmetics such as foundations, make-up bases, rouges, lipsticks, eye shadows, eye liners, mascaras, nail polishes, and so forth.

The hair cosmetics according to the present invention similarly contain the deodorized polyoxyalkylene-modified polysiloxane composition provided by the production method of the present invention and can be used in various forms. For example, these may be used dissolved or dispersed in an alcohol, hydrocarbon, volatile cyclic silicone, and so forth, or may be used in the form of an emulsion prepared by dispersion in water using an emulsifying agent. These may also be used as a spray in combination with a propellant such as propane, butane, trichloromonofluoromethane, dichlorodifluoromethane, dichlorotetrafluoroethane, carbon dioxide, nitrogen, and so forth. These formulations can be used as shampoos, rinses, set lotions, hair sprays, permanent wave agents, mousses, hair dyes, and so forth.

The components used in conventional cosmetic materials may be added to the cosmetic material of the present invention within a range that does not impair the effects of the present invention. These components can be exemplified by water, powders and colorants, alcohols, water-soluble polymers, film-forming agents, oils, oil-soluble gellants, organomodified clay minerals, surfactants, resins, ultraviolet absorbers, humectants, preservatives, antibacterials, fragrances, salts, antioxidants, pH adjusters, chelating agents, algefacients, antiinflammatories, skin beautifying components (whiteners, cell activators, agents for ameliorating skin roughness, circulation promoters, skin astringents, antiseborrheics, and so forth), vitamins, amino acids, nucleic acids, hormones, inclusion compounds, and so forth, as well as physiologically active substances and fragrances, but there is no particular limitation to the preceding.

The water should be clean and free of components toxic to humans and can be exemplified by tap water, purified water, and mineral water. When the cosmetic material of the present invention is a water-based cosmetic material, any water-soluble additive component can be incorporated in the aqueous phase within a range in which the effects of the present invention are not impaired. Water-soluble active substances, vide infra, such as vitamins, e.g., the vitamin B group, vitamin C and its derivatives, pantothenic acid and its derivatives, biotin, and so forth; water-soluble ultraviolet absorbers; and various water-soluble dyes can be incorporated as the components constituting the aqueous phase, but there is no limitation to the preceding. In addition, a known pH adjuster, preservative, antibacterial, or antioxidant can also be incorporated as appropriate with the goal of improving, for example, the storage stability of the cosmetic material.

Any powder or colorant used in conventional cosmetics can be used regardless of shape, e.g., spherical, rod-shaped, needle-shaped, plate-shaped, irregular, spindle-shaped, and so forth; particle size, e.g., aerosol, microparticulate, pigment grade, and so forth; and particle structure, e.g., porous, non-porous, and so forth. However, when these powders and/or colorants are incorporated as pigments, the incorporation is preferred of one or two or more selections from inorganic pigment powders, organic pigment powders, and resin powders that have an average particle size in the range from 1 nm to 20 μm.

The powder or colorant can be exemplified by inorganic powders, organic powders, metal salt powder surfactants, i.e., metal soaps, colored pigments, pearlescent pigments, organomodified clay minerals, metal powder pigments, and so forth; composites of these pigments may also be used. In specific terms, the inorganic powder can be exemplified by titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, muscovite, synthetic mica, phlogopite, lepidolite, biotite, lithia mica, silicic acid, silicic anhydride, aluminum silicate, sodium silicate, sodium magnesium silicate, magnesium silicate, aluminum magnesium silicate, calcium silicate, barium silicate, strontium silicate, metal salts of tungstic acid, hydroxyapatite, vermiculite, higilite, bentonite, montmorillonite, hectorite, zeolite, ceramic powders, calcium secondary phosphate, alumina, aluminum hydroxide, boron nitride, and so forth; the organic powder can be exemplified by polyamide powder, polyester powder, polyethylene powder, polypropylene powder, polystyrene powder, polyurethane powder, benzoguanamine powder, polymethylbenzoguanamine powder, polytetrafluoroethylene powder, polymethyl methacrylate powder, cellulose, silk powder, nylon powder, nylon 12, nylon 6, silicone powder, spherical silicone rubber powder, spherical silicone rubber powder having a surface coated by a polymethylsilsesquioxane, spherical polymethylsilsesquioxane powder, styrene.acrylic acid copolymer, divinylbenzene.styrene copolymer, vinyl resin, urea resin, phenolic resin, fluororesin, silicon resin, acrylic resin, melamine resin, epoxy resin, polycarbonate resin, microcrystalline fiber powder, starch powder, and lauroyllysine; the metal salt powder surfactant can be exemplified by zinc stearate, aluminum stearate, calcium stearate, magnesium stearate, zinc myristate, magnesium myristate, zinc palmitate, zinc laurate, zinc cetyl phosphate, calcium cetyl phosphate, and sodium zinc cetyl phosphate; the colored pigment can be exemplified by inorganic red pigments such as iron oxide red, iron oxide, iron hydroxide, and iron titanate, inorganic brown pigments such as γ-iron oxide, inorganic yellow pigments such as iron oxide yellow and ocher, inorganic black pigments such as iron oxide black and carbon black, inorganic purple pigments such as Manganese Violet and Cobalt Violet, inorganic green pigments such as chromium hydroxide, chromium oxide, cobalt oxide, and cobalt titanate, inorganic blue pigments such as Prussian blue and ultramarine blue, the lakes of tar dyes such as Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, and Orange No. 207, and the lakes of natural dyes such as carminic acid, laccaic acid, carthamin, brazilin, and crocin; the pearlescent pigment can be exemplified by titanium oxide-coated mica, titanium mica, iron oxide-treated titanium mica, titanium oxide-coated mica, bismuth oxychloride, titanium oxide-coated bismuth oxychloride, titanium oxide-coated talc, fish scale foil, and titanium oxide-coated colored mica; and the metal powder pigment can be exemplified by powders of metals such as aluminum, gold, silver, copper, platinum, and stainless steel.

The inorganic powder can also be particularly exemplified by powders that absorb and scatter ultraviolet radiation, e.g., finely divided titanium oxide, finely divided iron-containing titanium oxide, finely divided zinc oxide, finely divided cerium oxide, and composites of the preceding. More particularly, to provide an inorganic ultraviolet protective component, inter alia, the previously indicated inorganic powder pigments and metal powder pigments can be incorporated as agents that disperse ultraviolet radiation; this inorganic ultraviolet protective component can be exemplified by metal oxides such as titanium oxide, zinc oxide, cerium oxide, low-order titanium oxide, and iron-doped titanium oxide; metal hydroxides such as iron hydroxide; metal flake such as iron oxide plates and aluminum flake; and ceramics such as silicon carbide. Particularly preferred thereamong is at least one selection from finely divided metal oxides and finely divided metal hydroxides that have an average particle size in the range from 1 to 100 nm.

The organomodified clay minerals can be exemplified by dimethylbenzyldodecylammonium montmorillonite clay, dimethyldioctadecylammonium montmorillonite clay, dimethylalkylammonium hectorite, benzyldimethylstearylammonium hectorite, and distearyldimethylammonium chloride-treated aluminum magnesium silicate. Commercially available products here are Bentone 27, a benzyldimethylstearylammonium chloride-treated hectorite from the National Lead Co., and Bentone 38, a distearyldimethylammonium chloride-treated hectorite from the National Lead Co.

The spherical silicone rubber powder, also known as spherical silicone elastomer powder, preferably has a primary particle size in the range from 0.1 to 50 μm. Commercially available spherical silicone rubber powders can be exemplified by Torayfil E-506S, Torayfil E-508, 9701 Cosmetic Powder, and 9702 Powder, all from Dow Corning Toray Co., Ltd. The cosmetic material of the present invention may also use the spherical silicone rubber powder in the form of a water-based dispersion of the spherical silicone rubber powder. Such a water-based dispersion is commercially available as, for example, BY 29-129, PF-2001, and PIF Emulsion, all from Dow Corning Toray Co., Ltd.

In addition, these powders and colorants are particularly preferably subjected to a hydrophobing treatment. Composites may also be formed between these powders and/or colorants; a powder and/or colorant may be used that has been subjected to a surface treatment with, e.g., an ordinary oil, a silicone compound other than the polyoxyalkylene-modified polysiloxane composition according to the present invention, a fluorine compound, or a surfactant; and as necessary a single powder or colorant can be used or two or more powders and/or colorants can be used.

This hydrophobing treatment can be exemplified by treatment of the previously described powder and/or colorant with various hydrophobing surface-treatment agents, for example, treatment with an organosiloxane such as treatment with a methylhydrogenpolysiloxane, treatment with a silicone resin, treatment with a silicone gum, treatment with an acrylsilicone, and treatment with a fluorosilicone; treatment with a metal soap such as treatment with zinc stearate; treatment with a silane such as treatment with a silane coupling agent and treatment with an alkylsilane; treatment with a fluorine compound such as treatment with a perfluoroalkylsilane, a perfluoroalkyl phosphate ester salt, or a perfluoropolyether; treatment with an amino acid such as treatment with N-lauroyl-L-lysine; treatment with an oil such as treatment with squalane; and an acrylic treatment such as treatment with an alkyl acrylate. Combinations of more than one of these may also be used.

Particularly suitable for the powder or colorant under consideration is at least one powder or colorant selected from the group consisting of silicone resin powders, silicone rubber powders, organic resin powders excluding silicone resin powders, organomodified clay minerals, titanium oxide, zinc oxide, titanium mica, metal soaps, inorganic extender pigments, and inorganic colored pigments.

One or more selections from lower alcohols, sugar alcohols, and higher alcohols can be used as the alcohol. Specifically, the lower alcohols can be exemplified by ethanol, isopropanol, and so forth; the sugar alcohols can be exemplified by sorbitol, maltose, and so forth; and the higher alcohols can be exemplified by lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecynol, cholesterol, sitosterol, phytosterol, lanosterol, POE cholesterol ether, monostearyl glycerol ether (batyl alcohol), monooleyl glyceryl ether (selachyl alcohol), and so forth.

The water-soluble polymer is incorporated for the purpose of improving the use sensation provided by the cosmetic material and may be any amphoteric, cationic, anionic, or nonionic water-soluble polymer or water-swellable clay mineral as used in the usual cosmetic products. A single water-soluble polymer may be used or two or more may be used in combination. These water-soluble polymers have a thickening effect on a water-containing component and therefore are useful in particular for obtaining a gel-form water-containing cosmetic material, a water-in-oil cosmetic material emulsion, and an oil-in-water cosmetic material emulsion.

The amphoteric water-soluble polymer can be exemplified by amphoterized starch, dimethyldiallylammonium chloride derivatives such as, for example, acrylamide.acrylic acid.dimethyldiallylammonium chloride copolymers and acrylic acid.dimethyldiallylammonium chloride copolymers, and by methacrylic acid derivatives such as, for example, polymethacryloylethyldimethylbetaine and N-methacryloyloxy-ethyl-N,N-dimethylammonium-α-methylcarboxybetaine.alkyl methacrylate copolymers.

The cationic water-soluble polymer can be exemplified by quaternary nitrogen-modified polysaccharides, for example, cation-modified cellulose, cation-modified hydroxyethyl cellulose, cation-modified guar gum, cation-modified locust bean gum, and cation-modified starch; dimethyldiallylammonium chloride derivatives, for example, dimethyldiallylammonium chloride.acrylamide copolymers and polydimethylmethylenepiperidinium chloride; vinylpyrrolidone derivatives, for example, vinylpyrrolidone.dimethylaminoethyl methacrylate copolymer salts, vinylpyrrolidone.methacrylamidopropyltrimethylammonium chloride copolymers, and vinylpyrrolidone.methylvinylimidazolium chloride copolymers; and methacrylic acid derivatives, for example, methacryloylethyldimethylbetaine.methacryloylethyltrimethylammonium chloride.2-hydroxyethyl methacrylate copolymers and methacryloylethyldimethylbetaine.methacryloylethyltrimethylammonium chloride.methoxypolyethylene glycol methacrylate copolymers.

The anionic water-soluble polymer can be exemplified by the water-soluble polymers of aliphatic carboxylic acids and their metal salts, e.g., polyacrylic acid and its alkali metal salts, polymethacrylic acid and its alkali metal salts, hyaluronic acid and its alkali metal salts, acetylated hyaluronic acid and its alkali metal salts, and the hydrolyzates of methyl vinyl ether.maleic anhydride copolymers, as well as by carboxymethyl cellulose and its alkali metal salts, methyl vinyl ether-maleate hemiester copolymers, acrylic resin alkanolamine solutions, and carboxyvinyl polymers.

The nonionic water-soluble polymer can be exemplified by polyvinylpyrrolidone, highly polymerized polyethylene glycol, vinylpyrrolidone/vinyl acetate copolymers, vinylpyrrolidone/dimethylaminoethyl methacrylate copolymers, and vinylcaprolactam/vinylpyrrolidone/dimethylaminoethyl methacrylate copolymers and by natural polymer compounds such as cellulose and derivatives thereof, e.g., methyl cellulose, ethyl cellulose, hydroxyethyl cellulose, hydroxypropyl cellulose, carboxymethyl cellulose, and so forth, calcium alginate, pullulan, agar, gelatin, tamarind seed polysaccharides, xanthan gum, carrageenan, high methoxyl pectin, low methoxyl pectin, guar gum, pectin, gum arabic, crystalline cellulose, arabinogalactan, karaya gum, tragacanth gum, alginic acid, albumin, casein, curdlan, gellan gum, dextran, quince seed gum, traganth gum, chitin.chitosan derivatives, starch, e.g., rice, corn, potato, wheat, and so forth, and keratin and collagen and derivatives thereof.

The water-swellable clay mineral is an inorganic water-soluble polymer and is a type of colloid-containing aluminum silicate that has a trilayer structure, and can be generally exemplified by water-swellable clay minerals having the following formula (1)

$$(X,Y)_{2-3}(Si,Al)_4O_{10}(OH)_2Z_{1/3} \cdot nH_2O \tag{1}$$

wherein X is Al, Fe(III), Mn(III), or Cr(III); Y is Mg, Fe(II), Ni, Zn, or Li; and Z is K, Na, or Ca.

This inorganic water-soluble polymer can be specifically exemplified by bentonite, montmorillonite, beidellite, nontronite, saponite, hectorite, aluminum magnesium silicate, and silicic anhydride. These may be either the natural or synthetic material.

The oil may be any solid, semi-solid, or liquid oil as used in conventional cosmetics. This oil can be specifically exemplified by one or two or more selections from silicone oils, hydrocarbon oils, ester oils, plant oils and fats, animal oils and fats, liquid fatty acids, triglycerides, artificial sebum, and fluorooils.

The silicone oil can be specifically exemplified by the straight-chain organopolysiloxanes given by the following general formula (A1), the cyclic organopolysiloxanes given by general formula (A2), and the branched organopolysiloxanes given by general formula (A3).

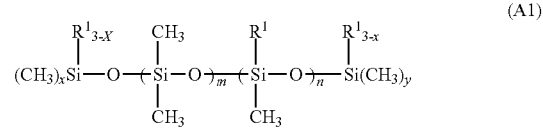

(A1)

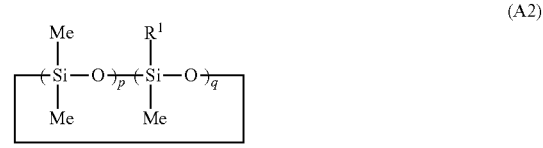

(A2)

(A3)

In general formulas (A1) to (A3) in the preceding paragraph, $R^1$ is a group selected from the hydrogen atom, the hydroxyl group, $C_{2-30}$ monovalent unsubstituted or fluorine-substituted alkyl groups, aryl groups, amino-substituted alkyl groups, alkoxy groups, and groups represented by $(CH_3)_3SiO\{(CH_3)_2SiO\}_u Si(CH_3)_2CH_2CH_2—$, and can be specifically exemplified by saturated aliphatic hydrocarbyl groups such as ethyl, propyl, butyl, pentyl, hexyl, heptyl, octyl, decyl, and dodecyl; unsaturated aliphatic hydrocarbyl groups such as vinyl, allyl, and hexenyl; saturated alicyclic hydrocarbyl groups such as cyclopentyl and cyclohexyl; aromatic hydrocarbyl groups such as phenyl, tolyl, and naphthyl; and groups provided by substituting a portion of the carbon-bonded hydrogen in the preceding groups with an organic group containing, e.g., a halogen atom, epoxy group, carboxyl group, amino group, methacryl group, mercapto group, and so forth, or provided by substituting a portion of the carbon-bonded hydrogen in the preceding groups with a trimethylsiloxy group bonded across a divalent hydrocarbyl group and/or a chain polydimethylsiloxane bond. m is an integer from 0 to 1000; n is an integer from 0 to 1000; m+n is an integer from 1 to 2000; x and y are 0, 1, 2, or 3; p and q are each integers from 0 to 8 wherein 3≤p+q≤8; r is an integer from 1 to 4; and u is an integer from 0 to 500.

Silicone oils having the structures described above can be specifically exemplified by cyclic organopolysiloxanes such as hexamethylcyclotrisiloxane (D3), octamethylcyclotetrasiloxane (D4), decamethylcyclopentasiloxane (D5), dodecamethylcyclohexasiloxane (D6), 1,1-diethylhexamethylcyclotetrasiloxane, phenylheptamethylcyclotetrasiloxane, 1,1-diphenylhexamethylcyclotetrasiloxane, 1,3,5,7-tetravinyltetramethylcyclotetrasiloxane, 1,3,5,7-tetramethylcyclotetrasiloxane, 1,3,5,7-tetracyclohexyltetramethylcyclotetrasiloxane, tris(3,3,3-trifluoropropyl)trimethylcyclotrisiloxane, 1,3,5,7-tetra(3-methacryloxypropyl)tetramethylcyclotetrasiloxane, 1,3,5,7-tetra(3-acryloxypropyl)tetramethylcyclotetrasiloxane, 1,3,5,7-tetra(3-carboxypropyl)tetramethylcyclotetrasiloxane, 1,3,5,7-tetra(3-vinyloxypropyl)tetramethylcyclotetrasiloxane, 1,3,5,7-tetra(p-vinylphenyl)tetramethylcyclotetrasiloxane, 1,3,5,7-tetra[3-(p-vinylphenyl)propyl]tetramethylcyclotetrasiloxane, 1,3,5,7-tetra(N-acryloyl-N-methyl-3-aminopropyl)tetramethylcyclotetrasiloxane, and 1,3,5,7-tetra(N,N-bis(lauroyl)-3-aminopropyl)tetramethylcyclotetrasiloxane, and by straight-chain organopolysiloxanes such as dimethylpolysiloxane endblocked at both molecular chain terminals by trimethylsiloxy, ranging from low viscosity dimethylsilicones at, for example, 2 cSt and 6 cSt, to high viscosity dimethylsilicones at, for example, 1,000,000 cSt, organohydrogenpolysiloxanes, methylphenylpolysiloxanes endblocked at both molecular chain terminals by trimethylsiloxy, dimethylsiloxane.methylphenylsiloxane copolymers endblocked at both molecular chain terminals by trimethylsiloxy, diphenylpolysiloxanes endblocked at both molecular chain terminals by trimethylsiloxy, dimethylsiloxane.diphenylsiloxane copolymers endblocked at both molecular chain terminals by trimethylsiloxy, trimethylpentaphenyltrisiloxane, phenyl(trimethylsiloxy)siloxane, methylalkylpolysiloxanes endblocked at both molecular chain terminals by trimethylsiloxy, dimethylpolysiloxane.methylalkylsiloxane copolymers endblocked at both molecular chain terminals by trimethylsiloxy, dimethylsiloxane.methyl(3,3,3-trifluoropropyl)siloxane copolymers endblocked at both molecular chain terminals by trimethylsiloxy, α,ω-dihydroxypolydimethylsiloxanes, α,ω-diethoxypolydimethylsiloxanes, 1,1,1,3,5,5,5-heptamethyl-3-octyltrisiloxane, 1,1,1,3,5,5,5-heptamethyl-3-dodecyltrisiloxane, 1,1,1,3,5,5,5-heptamethyl-3-hexadecyltrisiloxane, tristrimethylsiloxymethylsilane, tristrimethylsiloxyalkylsilane, tetrakistrimethylsiloxysilane, tetramethyl-1,3-dihydroxydisiloxane, octamethyl-1,7-dihydroxytetrasiloxane, hexamethyl-1,5-diethoxytrisiloxane, hexamethyldisiloxane, octamethyltrisiloxane, higher alcohol-modified silicones, and higher fatty acid-modified silicones.

The hydrocarbon oils can be exemplified by liquid paraffin, light liquid isoparaffin, heavy liquid isoparaffin, vaseline, n-paraffins, isoparaffins, isododecane, isohexadecane, polyisobutylene, hydrogenated polyisobutylene, polybutene, ozokerite, ceresin, microcrystalline wax, paraffin wax, polyethylene wax, polyethylene.polypropylene wax, squalane, squalene, pristane, polyisoprene, and so forth.

The ester oils can be exemplified by hexyldecyl octanoate, cetyl octanoate, isopropyl myristate, isopropyl palmitate, butyl stearate, hexyl laurate, myristyl myristate, oleyl oleate, decyl oleate, octyldodecyl myristate, hexyldecyl dimethyloctanoate, cetyl lactate, myristyl lactate, diethyl phthalate, dibutyl phthalate, lanolin acetate, ethylene glycol monostearate, propylene glycol monostearate, propylene glycol dioleate, glyceryl monostearate, glyceryl monooleate, glyceryl tri-2-ethylhexanoate, trimethylolpropane tri-2-ethylhexanoate, ditrimethylolpropane triethylhexanoate, ditrimethyloipropane isostearate/sebacate, trimethylolpropane trioctanoate, trimethylolpropane triisostearate, diisopropyl adipate, diisobutyl adipate, 2-hexyldecyl adipate, di-2-heptylundecyl adipate, diisostearyl malate, hydrogenated castor oil monoisostearate, n-alkylglycol monoisostearate, octyldodecyl isostearate, isopropyl isostearate, isocetyl isostearate, ethylene glycol di-2-ethylhexanoate, cetyl 2-ethylhexanoate, pentaerythritol tetra-2-ethylhexanoate, octyldodecyl gum ester, ethyl oleate, octyldodecyl oleate, neopentyl glycol dicaprate, triethyl citrate, 2-ethylhexyl citrate, dioctyl citrate, isocetyl stearate, diisopropyl sebacate, di-2-ethylhexyl sebacate, diethyl sebacate, dioctyl sebacate, dibutyloctyl sebacate, cetyl palmitate, octyldodecyl palmitate, octyl palmitate, 2-ethylhexyl palmitate, 2-hexyldecyl palmitate, 2-heptylundecyl palmitate, cholesteryl 12-hydroxystearate, esters between dipentaerythritol and fatty acids, 2-hexyldecyl myristate, ethyl laurate, 2-octyldodecyl N-lauroyl-L-glutamate, di(cholesteryl/behenyl/octyldodecyl) N-lauroyl-L-glutamate, di(cholesteryl/octyldodecyl) N-lauroyl-L-glutamate, di(phytosteryl/behenyl/octyldodecyl) N-lauroyl-L-glutamate, di(phytosteryl/octyldodecyl) N-lauroyl-L-glutamate, isopropyl N-lauroylsarcosinate, diisostearyl malate, neopentyl glycol dioctanoate, isodecyl neopentanoate, isotridecyl neopentanoate, isostearyl neopentanoate, isononyl isononanoate, isotridecyl isononanoate, octyl isononanoate, isotridecyl isononanoate, diethylpentanediol dineopentanoate, methylpentanediol dineopentanoate, octyldodecyl neodecanoate, 2-butyl-2-ethyl-1,3-propanediol dioctanoate, pentaerythrityl tetraoctanoate, pentaerythrityl hydrogenated rosin, pentaerythrityl triethylhexanoate, dipentaerythrityl (hydroxystearate/stearate/rosinate), polyglyceryl tetraisostearate, polyglyceryl-10 nonaisostearate, polyglyceryl-8 deca(erucate/isostearate/ricinoleate), diglyceryl (hexyldecanoate/sebacate) oligoester, glycol distearate (ethylene glycol distearate), diisopropyl dimer dilinoleate, diisostearyl dimer dilinoleate, di(isostearyl/phytosteryl) dimer dilinoleate, (phytosteryl/behenyl) dimer dilinoleate, (phytosteryl/isostearyl/cetyl/stearyl/behenyl) dimer dilinoleate, dimer dilinoleyl dimer dilinoleate, dimer dilinoleyl diisostearate, dimer dilinoleyl hydrogenated rosin condensate, hydrogenated castor oil dimer dilinoleate, hydroxyalkyl dimer dilinoleyl ether, glyceryl triisooctanoate, glyceryl triisostearate, glyceryl trimyristate, glyceryl triisopalmitate, glyceryl trioctanoate, glyceryl trioleate, glyceryl diisostearate, glyceryl tri(caprylate/caprate), glyceryl tri(caprylate/caprate/myristate/stearate), hydrogenated rosin triglyceride (hydrogenated ester gum), rosin triglyceride (ester gum), glyceryl behenate eicosanedioate, glyceryl di-2-heptylundecanoate, diglyceryl myristate isostearate, cholesteryl acetate, cholesteryl nonanoate, cholesteryl stearate, cholesteryl isostearate, cholesteryl oleate, cholesteryl 12-hydroxystearate, cholesteryl esters of macadamia nut oil fatty acids, phytosteryl esters of macadamia nut oil fatty acids, phytosteryl isostearate, cholesteryl esters of soft lanolin fatty acids, cholesteryl esters of hard lanolin fatty acids, cholesteryl esters of long-chain branched fatty acids, cholesteryl esters of long-chain α-hydroxyfatty acids, octyldodecyl ricinoleate, octyldodecyl esters of lanolin fatty acids, octyldodecyl erucate, hydrogenated castor oil isostearate, ethyl esters of avocado oil fatty acids, and isopropyl esters of lanolin fatty acids.

The plant and animal oils and fats of natural origin and semisynthetic oils and fats can be exemplified by avocado oil, linseed oil, almond oil, *Ericerus pela* (Chavannes) wax, perilla oil, olive oil, cacao butter, Kapok tree wax, kaya oil, carnauba wax, cod liver oil, candelilla wax, beef tallow, hoof oil, cow bone fat, hardened beef tallow, apricot kernel oil, spermaceti wax, hardened oils, wheat germ oil, sesame oil, rice germ oil, rice bran oil, sugarcane wax, camellia Kissi seed oil, safflower oil, shea butter, Paulownia oil, cinnamon oil, jojoba wax, olive squalane, shellac wax, turtle oil, soybean oil, tea seed oil, camellia oil, evening primrose oil, corn oil, lard, rape-seed oil, Japanese tung oil, bran wax, germ oil, horse fat, persic oil, palm oil, palm kernel oil, castor oil, hardened castor oil, methyl esters of castor oil fatty acids, sunflower oil, grape seed oil, bayberry wax, jojoba oil, hydrogenated jojoba esters, macadamia nut oil, yellow beeswax, mink oil, cottonseed oil, cotton wax, Japan wax, sumac kernel oil, montan wax, coconut oil, hardened coconut oil, cocofatty acid triglycerides, mutton tallow, peanut oil, lanolin, liquid lanolin, reduced lanolin, lanolin alcohol, hardened lanolin, lanolin acetate, isopropyl esters of lanolin fatty acids, POE lanolin alcohol ethers, POE lanolin alcohol acetate, polyethylene glycol esters of lanolin fatty acids, POE hydrogenated lanolin alcohol ethers, yolk oil, and so forth. Here, POE denotes polyoxyethylene.

The higher fatty acids can be exemplified by lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid, 12-hydroxystearic acid, and so forth.

The fluorooils can be exemplified by perfluoropolyethers, perfluorodecalin, perfluorooctane, and so forth. As necessary, a single one of these oils or two or more of these oils can be used.

The oil-soluble gellant can be exemplified by metal soaps such as aluminum stearate, magnesium stearate, and zinc myristate; amino acid derivatives such as N-lauroyl-L-glutamic acid and $\alpha,\gamma$-di-n-butylamine; dextrin fatty acid esters such as dextrin palmitate, dextrin stearate, and dextrin 2-ethylhexanoate palmitate; sucrose fatty acid esters such as sucrose palmitate and sucrose stearate; fructooligosaccharide fatty acid esters such as inulin stearate and fructooligosaccharide 2-ethylhexanoate; the benzylidene derivatives of sorbitol, such as monobenzylidene sorbitol and dibenzylidene sorbitol; and organomodified clay minerals such as dimethylbenzyldodecylammonium montmorillonite clay and dimethyldioctadecylammonium montmorillonite clay. As necessary, a single one of these can be used or two or more can be used.

The cosmetic material of the present invention may incorporate a surfactant other than the previously indicated components. This surfactant can be a single surfactant or a combination of two or more surfactants selected from the group consisting of silicone-type surfactants other than the polyoxyalkylene-modified polysiloxane composition according to the present invention, anionic surfactants, cationic surfactants, nonionic surfactants, amphoteric surfactants, and semipolar surfactants.

The silicone-type surfactant is a silicone-type surfactant other than the polyoxyalkylene-modified polysiloxane composition according to the present invention. This silicone-type surfactant is an oil-emulsifying component or is a cleansing component, and representative examples are polyglyceryl-modified silicones, glyceryl-modified silicones, and sugar-modified silicones.

The anionic surfactant can be exemplified by saturated and unsaturated fatty acid salts, e.g., sodium laurate, sodium stearate, sodium oleate, sodium linolenate, and so forth; alkyl sulfate salts; alkylbenzenesulfonic acids, e.g., hexylbenzenesulfonic acid, octylbenzenesulfonic acid, dodecylbenzenesulfonic acid, and so forth, and their salts; polyoxyalkylene alkyl ether sulfate salts; polyoxyalkylene alkenyl ether sulfate salts; polyoxyethylene alkyl sulfate ester salts; the salts of alkyl sulfosuccinate esters; polyoxyalkylene sulfosuccinate alkyl ester salts; polyoxyalkylene alkylphenyl ether sulfate salts; octyltrimethylammonium hydroxide; dodecyltrimethylammonium hydroxide; alkylsulfonate; polyoxyethylene alkylphenyl ether sulfate salts; polyoxyalkylene alkyl ether acetate salts; alkyl phosphate salts; polyoxyalkylene alkyl ether phosphate salts; acylglutamic acid salts; $\alpha$-acylsulfonic acid salts; alkylsulfonate salts; alkylallylsulfonate salts; $\alpha$-olefinsulfonate salts; alkylnaphthalenesulfonate salts; alkanesulfonate salts; alkyl or alkenyl sulfate salts; alkylamide sulfate salts; alkyl or alkenyl phosphate salts; alkylamide phosphate salts; alkyloylalkyltaurine salts; N-acylamino acid salts; sulfosuccinate salts; alkyl ether carboxylate salts; amide ether carboxylate salts; $\alpha$-sulfofatty acid ester salts; alanine derivatives; glycine derivatives; and arginine derivatives. The salts can be exemplified by alkali metal salts, e.g., sodium and so forth; alkaline-earth metal salts, e.g., magnesium and so forth; alkanolamine salts such as the triethanolamine salt and so forth; and ammonium salts.

The cationic surfactant can be exemplified by alkyltrimethylammonium chloride, stearyltrimethylammonium chloride, lauryltrimethylammonium chloride, cetyltrimethylammonium chloride, beef tallow alkyltrimethylammonium chloride, behenyltrimethylammonium chloride, stearyltrimethylammonium bromide, behenyltrimethylammonium bromide, distearyldimethylammonium chloride, dicocoyldimethylammonium chloride, dioctyldimethylammonium chloride, di(POE)oleylmethylammonium chloride (2EO), benzalkonium chloride, alkylbenzalkonium chloride, alkyldimethylbenzalkonium chloride, benzethonium chloride, stearyldimethylbenzylammonium chloride, lanolin-derived quaternary ammonium salts, the diethylaminoethylamide of stearic acid, the dimethylaminopropylamide of stearic acid, behenamidepropyl dimethyl hydroxypropyl ammonium chloride, (stearoylcolaminoformylmethyl)pyridinium chloride, cetylpyridinium chloride, tall oil alkylbenzylhydroxyethylimidazolinium chloride, and benzylammonium salts.

The nonionic surfactant can be exemplified by polyoxyalkylene ethers, polyoxyalkylene alkyl ethers, polyoxyalkylene fatty acid esters, polyoxyalkylene fatty acid diesters, polyoxyalkylene resin acid esters, polyoxyalkylene (hydrogenated) castor oils, polyoxyalkylene alkylphenols, polyoxyalkylene alkylphenyl ethers, polyoxyalkylene phenylphenyl ethers, polyoxyalkylene alkyl esters, polyoxyalkylene alkyl esters, sorbitan fatty acid esters, polyoxyalkylene sorbitan alkyl esters, polyoxyalkylene sorbitan fatty acid esters, polyoxyalkylene sorbitol fatty acid esters, polyoxyalkylene glycerol fatty acid esters, polyglycerol alkyl ethers, polyglycerol fatty acid esters, sucrose fatty acid esters, fatty acid alkanolamides, alkylglucosides, polyoxyalkylene fatty acid bisphenyl ethers, polypropylene glycols, diethylene glycol, polyoxyalkylene-modified silicones, polyglyceryl-modified silicones, glyceryl-modified silicones, saccharide-modified silicones, fluorosurfactants, polyoxyethylene.polyoxypropylene block polymers, and alkyl polyoxyethylene.polyoxypropylene block polymer ethers.

The amphoteric surfactant can be exemplified by imidazoline-type, amidobetaine-type, alkylbetaine-type, alkylamidobetaine-type, alkylsulfobetaine-type, amidosulfobetaine-type, hydroxysulfobetaine-type, carbobetaine-type, phosphobetaine-type, aminocarboxylic acid-type, and amidoamino acid-type amphoteric surfactants. Specific examples are imidazoline-type amphoteric surfactants such as sodium 2-undecyl-N,N,N-(hydroxyethylcarboxymethyl)-2-imidazoline and 2-cocoyl-2-imidazolinium hydroxide-1-carboxyethyloxy disodium salt; alkylbetaine-type amphoteric surfactants such as lauryldimethylaminoacetic acid betaine and myristyl betaine; amidobetaine-type amphoteric surfactants such as cocofatty acid amidopropyldimethylaminoacetic acid betaine, palm kernel oil fatty acid amidopropyldimethylaminoacetic acid betaine, beef tallow fatty acid amidopropyldimethylaminoacetic acid betaine, hydrogenated beef tallow fatty acid amidopropyldimethylaminoacetic acid betaine, lauric acid amidopropyldimethylaminoacetic acid betaine, myristic acid amidopropyldimethylaminoacetic acid betaine, palmitic acid amidopropyldimethylaminoacetic acid betaine, stearic acid amidopropyldimethylaminoacetic acid betaine, and oleic acid amidopropyldimethylaminoacetic acid betaine; alkylsulfobetaine-type amphoteric surfactants such as cocofatty acid dimethylsulfopropylbetaine; alkylhydroxysulfobetaine-type amphoteric surfactants such as lauryldimethylaminohydroxysulfobetaine; phosphobetaine-type amphoteric surfactants such as laurylhydroxyphosphobetaine; and amidoamino acid-type amphoteric surfactants such as sodium N-lauroyl-N'-hydroxyethyl-N'-carboxymethylethylenediamine, sodium N-oleoyl-N'-hydroxyethyl-N'-carboxymethylethylenediamine, sodium N-cocoyl-N'-hydroxyethyl-N'-carboxymethylethylenediamine, potassium N-lauroyl-N'-hydroxyethyl-N'-carboxymethylethylenediamine, potassium N-oleoyl-N'-hydroxyethyl-N'-carboxymethylethylenediamine, sodium N-lauroyl-N-hydroxyethyl-N'-carboxymethylethylenediamine, sodium N-oleoyl-N-hydroxyethyl-N'-carboxymethylethylenediamine, sodium N-cocoyl-N-hydroxyethyl-N'-carboxymethylethylenediamine, monosodium N-lauroyl-N-hydroxyethyl-N',N'-dicarboxymethylethylenediamine, monosodium N-oleoyl-N-hydroxyethyl-N',N'-dicarboxymethylethylenediamine, monosodium N-cocoyl-N-hydroxyethyl-N',N'-dicarboxymethylethylenediamine, disodium N-lauroyl-N-hydroxyethyl-N',N'-dicarboxymethylethylenediamine, disodium N-oleoyl-N-hydroxyethyl-N',N'-dicarboxymethylethylenediamine, and disodium N-cocoyl-N-hydroxyethyl-N',N'-dicarboxymethylethylenediamine.

The semi-polar surfactant can be exemplified by alkylamine oxide-type surfactants, for example, alkylamine oxides, alkylamidoamine oxides, and alkylhydroxyamine oxides, wherein $C_{10-18}$ alkyldimethylamine oxides and $C_{8-18}$ alkoxyethyldihydroxyethylamine oxides are preferably used. Specific examples are dodecyldimethylamine oxide, dimethyloctylamine oxide, diethyldecylamine oxide, bis(2-hydroxyethyl)dodecylamine oxide, dipropyltetradecylamine oxide, methylethylhexadecylamine oxide, dodecylamidopropyldimethylamine oxide, cetyldimethylamine oxide, stearyldimethylamine oxide, tallow dimethylamine oxide, dimethyl-2-hydroxyoctadecylamine oxide, lauryldimethylamine oxide, myristyldimethylamine oxide, stearyldimethylamine oxide, isostearyldimethylamine oxide, cocofatty acid alkyldimethylamine oxide, caprylic acid amidopropyldimethylamine oxide, capric acid amidopropyldimethylamine oxide, lauric acid amidopropyldimethylamine oxide, myristic acid amidopropyldimethylamine oxide, palmitic acid amidopropyldimethylamine oxide, stearic acid amidopropyldimethylamine oxide, isostearic acid amidopropyldimethylamine oxide, oleic acid amidopropyldimethylamine oxide, ricinoleic acid amidopropyldimethylamine oxide, 12-hydroxystearic acid amidopropyldimethylamine oxide, cocofatty acid amidopropyldimethylamine oxide, palm kernel oil fatty acid amidopropyldimethylamine oxide, castor oil fatty acid amidopropyldimethylamine oxide, lauric acid amidoethyldimethylamine oxide, myristic acid amidoethyldimethylamine oxide, cocofatty acid amidoethyldimethylamine oxide, lauric acid amidoethyldiethylamine oxide, myristic acid amidoethyldiethylamine oxide, cocofatty acid amidoethyldiethylamine oxide, lauric acid amidoethyldihydroxyethylamine oxide, myristic acid amidoethyldihydroxyethylamine oxide, and cocofatty acid amidoethyldihydroxyethylamine oxide.

The ultraviolet protective agents include inorganic ultraviolet protective agents and organic ultraviolet protective agents. When the cosmetic material of the present invention is a sunscreen cosmetic material, it preferably contains at least one organic ultraviolet protective agent, while the use of the combination of an ultraviolet protective component effective against UV-A with an ultraviolet protective component effective against UV-B is more preferred.

For the inorganic ultraviolet protective component, inter alia, an inorganic powder pigment or metal powder pigment can be incorporated as an agent that disperses ultraviolet radiation; this inorganic ultraviolet protective component can be exemplified by metal oxides such as titanium oxide, zinc oxide, cerium oxide, low-order titanium oxide, and iron-doped titanium oxide; metal hydroxides such as iron hydroxide; metal flake such as iron oxide plates and aluminum flake; and ceramics such as silicon carbide.

The organic ultraviolet protective component can be exemplified by benzoic acid-type ultraviolet absorbers such as para-aminobenzoic acid and so forth, anthranilic acid-type ultraviolet absorbers such as methyl anthranilate and so forth, salicylic acid-type ultraviolet absorbers such as methyl salicylate and so forth, cinnamic acid-type ultraviolet absorbers such as octyl p-methoxycinnamate and so forth, benzophenone-type ultraviolet absorbers such as 2,4-dihydroxybenzophenone and so forth, urocanic acid-type ultraviolet absorbers such as ethyl urocanate and so forth, and dibenzoylmethane-type ultraviolet absorbers such as 4-t-butyl-4'-methoxydibenzoylmethane and so forth.

The humectant can be a polyhydric alcohol such as glycerol, sorbitol, propylene glycol, dipropylene glycol, 1,3-butylene glycol, glucose, xylitol, maltitol, polyethylene glycol, and so forth, or hyaluronic acid, chondroitin sulfate, a salt of pyrrolidonecarboxylic acid, polyoxyethylene methyl glucoside, polyoxypropylene methyl glucoside, and so forth.

The antibacterial preservative can be exemplified by alkyl para-hydroxybenzoate esters, benzoic acid, sodium benzoate, sorbic acid, potassium sorbate, phenoxyethanol, and so forth, while the antibacterial can be exemplified by benzoic acid, salicylic acid, carbolic acid, sorbic acid, alkyl para-hydroxybenzoate esters, p-chloro-m-cresol, hexachlorophene, benzalkonium chloride, chlorhexidine chloride, trichlorocarbanilide, triclosan, photosensitive ingredients, phenoxyethanol, and so forth. These are preferably not incorporated in lipsticks.

The antioxidant can be exemplified by tocopherol, butylhydroxyanisole, dibutylhydroxytoluene, phytic acid, and so forth.

The pH adjuster can be exemplified by lactic acid, citric acid, glycolic acid, succinic acid, tartaric acid, dl-malic acid, potassium carbonate, sodium bicarbonate, ammonium bicarbonate, and so forth.

The chelating agent can be exemplified by alanine, sodium edetate, sodium polyphosphate, sodium meta-phosphate, phosphoric acid, and so forth.

The algefacient can be exemplified by L-menthol, camphor, and so forth, while the antiinflammatory can be exemplified by allantoin, glycyrrhetinic acid, glycyrrhizic acid, tranexamic acid, azulene, and so forth.

The skin beautifying component can be exemplified by whiteners such as placental extract, arbutin, glutathione, Saxifraga sarmentosa extract, and so forth; cell activators such as royal jelly; agents for ameliorating skin roughness; circulation promoters such as nonylic acid valenylamide, benzyl nicotinate, β-butoxyethyl nicotinate, capsaicin, zingerone, Cantharides tincture, ichthammol, caffeine, tannic acid, α-borneol, tocopherol nicotinate, inositol hexanicotinate, cyclandelate, cinnarizine, tolazoline, acetylcholine, verapamil, cepharanthine, γ-oryzanol, and so forth; skin astringents such as zinc oxide, tannic acid, and so forth; and antiseborrheics such as sulfur, thianthrol, and so forth. The vitamins can be exemplified by vitamin A species such as vitamin A oil, retinol, retinol acetate, and retinol palmitate; vitamin B species such as vitamin B2 species such as riboflavin, riboflavin butyrate, and flavin adenine nucleotide, vitamin B6 species such as pyridoxine hydrochloride, pyridoxine dioctanoate, and pyridoxine tripalmitate, vitamin B12 and derivatives thereof, and vitamin B15 and derivatives thereof; vitamin C species such as L-ascorbic acid, L-ascorbic acid dipalmitic acid ester, sodium L-ascorbic acid-2-sulfate, and dipotassium L-ascorbic acid phosphoric acid diester; vitamin D species such as ergocalciferol and cholecalciferol; vitamin E species such as α-tocopherol, β-tocopherol, γ-tocopherol, dl-α-tocopherol acetate, dl-α-tocopherol nicotinate, and dl-α-tocopherol succinate; vitamin H; nicotinic acids such as vitamin P, nicotinic acid, and benzyl nicotinate; and pantothenic acids such as calcium pantothenate, D-pantothenyl alcohol, pantothenyl ethyl ether, and acetylpantothenyl ethyl ether.

The amino acid can be exemplified by amino acids such as glycine, valine, leucine, isoleucine, serine, threonine, phenylalanine, arginine, lysine, aspartic acid, glutamic acid, cystine, cysteine, methionine, tryptophan, and so forth, and/or by their salts.

The nucleic acid can be exemplified by deoxyribonucleic acid and so forth, while the hormone can be exemplified by estradiol, ethenylestadiol, and so forth.

The physiologically active component is, for example, a lipophilic substance that, when applied to the skin, imparts some physiological activity to the skin. Examples are antiinflammatories, ageing inhibitors, pore-tightening agents, hair-restoring agents, hair-growth agents, humectants, circulation promoters, desiccants, calorifacient agents, vitamins, wound-healing promoters, anti-irritants, analgesics, cell activators, enzyme components, and so forth. Similarly, a natural plant extract component, seaweed extract component, or herbal medicine component may preferably be incorporated.

The fragrance is any lipophilic fragrance and is not otherwise particularly limited, and can be exemplified by fragrances extracted from, inter alia, the flower, seed, leaf, and root of plants; fragrances extracted from seaweed; fragrances extracted from various animal parts and secretions, e.g., musk and incense; and artificially synthesized fragrances, e.g., menthol, musk, acetate esters, and vanilla. The fragrance is incorporated in order to impart fragrance or aroma to the cosmetic material. The colorant can be, for example, an oil-soluble dye, extender pigment, inorganic pigment, organic pigment, or lipophilic fluorescent whitener.

EXAMPLES

The present invention is described in even greater detail by the examples provided herebelow, but the present invention is not limited by these examples. The methylhydrogenpolysiloxane used in the reference examples was produced by an equilibration reaction using a standard method. The following methods were used to evaluate the odor (odor test) of the purified polyoxyalkylene-modified polysiloxane composition (the polyoxyalkylene-modified polysiloxane composition is referred to below as the "sample") and to evaluate the presence/absence of cleavage of the silicon-oxygen bond (Si—O) in the polysiloxane moiety.

[Odor Test 1: Measurement of the Total Quantity of Carbonyl]

The "carbonyl value (CV)" of the polyoxyalkylene-modified polysiloxane composition was determined by applying the <Measurement (A) of the Total Quantity of Carbonyl in the Composition> described in JP 2005-120293 A, modified as necessary. Specifically, the carbonyl value, which causes odor, was quantitatively evaluated for the composition by measuring the "carbonyl value (CV)" of the polyoxyalkylene-modified polysiloxane composition using the following procedure.

<Measurement (A) of the Total Quantity of Carbonyl in the Composition>

The total quantity of carbonyl was measured using the following measurement method (measurement of the carbonyl value.measurement of the calibration curve.carbonyl determination) for each polyoxyalkylene-modified polysiloxane composition (sample) in the examples and comparative examples. The "ultrahigh purity alcohol (A)" used for the reaction solvent and dilution solvent was a commercial product that had been produced 3 months prior to use ("Ethanol (99.8) Infinity Pure" from Wako Pure Chemical Industries, Ltd.) and was unsealed immediately prior to use (total aldehyde.ketone=2.4 to 2.9 ppm).

Production Example 1A

A bottle holding 100 mL of the ultrahigh purity alcohol (A) was unsealed and 4.30 g special reagent grade trichloroacetic acid was immediately added to the bottle. The bottle was then re-capped and was thereafter mixed by shaking to achieve uniformity and produce an alcohol solution of trichloroacetic acid that had an acid concentration of 4.3% (wt/vol). This solution was designated as "trichloroacetic acid solution (1A)". This production process was carried out within one hour prior to the absorbance measurement.

Production Example 2A

A bottle holding 100 mL of the ultrahigh purity alcohol (A) was unsealed and 50 mg 2,4-dinitrophenylhydrazine (special reagent grade product containing an equal amount of water, referred to below as "2,4-DNPH") was immediately added to the bottle. The bottle was then re-capped and the 2,4-DNPH was completely dissolved in the ultrahigh purity alcohol (A) by holding for 5 minutes in an ultrasound cleaner to produce an alcohol solution of 0.025% (wt/vol) 2,4-DNPH. This solution was designated as "2,4-DNPH solution (2A)". This production process was carried out within one hour prior to the absorbance measurement.

Production Example 3A

A bottle holding 100 mL of the ultrahigh purity alcohol (A) was unsealed and 4.0 g potassium hydroxide (pellets, special reagent grade) was immediately added to the bottle. The bottle was then re-capped; mixing by shaking was performed until the pellets had disappeared; and the potassium hydroxide was then completely dissolved in the ultrahigh purity alcohol (A) by holding for 10 minutes in an ultrasound cleaner to produce an alcohol solution of 4.0% (wt/vol) potassium hydroxide. This solution was designated as "potassium hydroxide solution (3A)". This production process was carried out within one hour prior to the absorbance measurement.

[Measurement of the Carbonyl Value]

2.00 g sample and 23.00 g ultrahigh purity alcohol (A) were introduced into a 50-mL screw-cap bottle and were mixed to prepare 25.00 g of a sample solution (Sa) having a sample concentration of 8 mass %. The compositions obtained in Comparative Examples 1, 3, 4, 5, and 6 had very high carbonyl values, and, when the procedure was continued using a sample solution (Sa) having a sample concentration of 8 mass %, the absorbance ($A_1$) exceeded 0.80, which indicated that an accurate absorbance measurement could not be performed. Due to this, sample solutions were prepared from the compositions obtained in Comparative Examples 1, 3, 4, 5, and 6 by introducing 0.200 g sample and 24.80 g ultrahigh purity alcohol (A) into a 50-mL screw-cap bottle and mixing to prepare a solution that had a sample concentration of 0.8 mass %, which was then used as sample solution (Sa).

1.250 g of the obtained sample solution (Sa) and 3.750 g high purity alcohol (A) were introduced into a 50-mL volumetric flask and the two were mixed to prepare 5.000 g of a sample solution (Sb) that had a sample concentration of 2 mass %.

3 mL of the trichloroacetic acid solution (1A) obtained in Production Example 1A and 5 mL of the 2,4-DNPH solution (2A) obtained in Production Example 2A were added using a whole pipette to the volumetric flask holding the 5.000 g of sample solution (Sb). 1.050 g purified water was also added and mixing was carried out. The volumetric flask was then stoppered and securely sealed by wrapping the stopper with Teflon (registered trademark) tape. The volumetric flask was then introduced into a 60° C. thermostat and was heated for 30 minutes to react the 2,4-DNPH with the carbonyl present in the sample.

The volumetric flask was subsequently removed from the thermostat and held for 30 minutes at room temperature. The volumetric flask was then unstoppered and 10 mL of the potassium hydroxide solution (3A) obtained in Production Example 3A was added using a whole pipette and mixing was performed by shaking the volumetric flask.

At 8 minutes after the addition of the 10 mL potassium hydroxide solution (3A), the ultrahigh purity alcohol (A) was added as a dilution solvent and this system was mixed by shaking to prepare a total of 50 mL of a reaction solution (basic reaction solution). At 15 minutes after the addition of the 10 mL potassium hydroxide solution (3A), this reaction solution, from which the turbidity had been removed, was introduced into an absorption cell (length of liquid layer=1 cm) and the absorbance ($A_1$) at 430 nm was measured using an absorption spectrophotometer.

In the blank test, 5.000 g ultrahigh purity alcohol (A) was used in place of the test solution (Sb) and a solution was then prepared by the same procedure as described above, i.e., addition of the trichloroacetic acid solution (1A), addition of the 2,4-DNPH solution (2A), heating and cooling of the obtained mixed solution, addition of the potassium hydroxide solution (3A), and addition of the ultrahigh purity alcohol (A) dilution solvent). The obtained solution was introduced into an absorption cell (length of liquid layer=1 cm) and the absorbance ($A_2$) at 430 nm was measured proceeding as described above.

The carbonyl value (CV) was determined by substituting the absorbance ($A_1$) and absorbance ($A_2$) obtained as described above into the expression $CV=(A_1-A_2)/0.1$.

In the case of the samples prepared from the compositions obtained in Comparative Examples 1, 3, 4, 5, and 6, the carbonyl value was determined by substitution into the expression $CV=(A_1-A_2)/0.01$.

[Odor Test 2: Evaluation of the Odor of a Blended System]

Using a mixed system of the particular polyoxyalkylene-modified polysiloxane composition with water/(polyhydric) alcohol as a model cosmetic blended system, the level of odor was monitored with elapsed time in order to evaluate the inhibitory action on odor generation with elapsed time. Here, the mixed system with water/(polyhydric) alcohol was prepared by introducing 3.0 g sample, 3.0 g propylene glycol, and 24.0 g purified water into a 50-mL screw-cap bottle and capping and mixing by shaking. The odor generation with elapsed time was evaluated using the scale given below in the initial period of mixing, i.e., immediately after mixing, and after standing for 2 weeks in a 70° C. atmosphere.

++: almost no perception of odor

+: very weak perception of odor (characteristic ethereal odor)

Δ: weak perception of odor (characteristic ethereal odor)

x: strong perception of odor (characteristic ethereal odor)

[Presence/Absence of Cleavage of the Silicon-Oxygen Bond (Si—O) in the Polysiloxane Moiety]

The product was analyzed by $^{29}$Si-NMR in order to check whether cleavage of the silicon-oxygen bond had occurred in the organopolysiloxane moiety of the particular polyoxyalkylene-modified polysiloxane composition. Based on the fact that silanol (≡Si—O—H) is formed when this cleavage has occurred, the determination was carried out based on the presence/absence of a signal in $^{29}$Si-NMR for $^{29}$Si attributed to this silanol group in the −15 to −10 ppm region using deuterated benzene for the solvent.

[Conditions in the Stripping Step]

Operating under a nitrogen feed, the interior was evacuated and the temperature was raised to 80 to 90° C. and the low-boiling fraction (propionaldehyde and so forth) was removed over 1 to 3 hours at 1 to 4 kPa (stripping step).

Practical Example 1

The following were introduced into a 1000-mL (1 L) four-neck flask equipped with a stirrer, reflux condenser, thermometer, and nitrogen inlet port: 500 g of a methylhydrogenpolysiloxane with the structural formula $(CH_3)_3SiO[(CH_3)_2SiO]_{45}[(CH_3)HSiO]_2Si(CH_3)_3$ that exhibited a hydrogen gas production of 12.2 mL/g; 200 g of an allyl polyether with the structural formula $CH_2=CHCH_2O(C_2H_4O)_{10}H$; and 200 g isopropyl alcohol (IPA). To this was added a platinum/divinyltetramethyldisiloxane-toluene solution having a platinum concentration of 3.0 mass %, and a reaction was run for 3 hours at 80° C.

The low-boiling fraction was then distilled out under reduced pressure followed by the addition of 0.035 g sodium bisulfate monohydrate and 11 g purified water. A hydrolysis treatment was performed for 1 hour at 80° C. followed by the distillative removal of the low-boiling fraction under reduced pressure.

An additional 11 g purified water was added and a hydrolysis treatment was performed for 3 hours at 80° C., followed by distillative removal of the low-boiling fraction under reduced pressure proceeding as previously described. The obtained reaction product was cooled to room temperature and returned to ambient pressure and was mixed with 10 g diatomaceous earth and a solid/liquid separation process (removal of the catalyst) was performed by carrying out a pressure filtration. A "polyoxyalkylene-modified polysiloxane composition 1" was obtained as the filtrate provided by this process.

Practical Example 2

The following were introduced into a 1000-mL (1 L) four-neck flask equipped with a stirrer, reflux condenser, thermometer, and nitrogen inlet port: 171 g of a methylhydrogenpolysiloxane with the structural formula

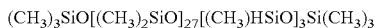

that exhibited a hydrogen gas production of 28.7 mL/g and 529 g of an allyl polyether with the structural formula $CH_2=CHCH_2O(C_2H_4O)_{19}(C_3H_6O)_{19}H$. To this was added a platinum/divinyltetramethyldisiloxane-toluene solution having a platinum concentration of 3.0 mass %, and a reaction was run for 2 hours at 80° C.

0.175 g ammonium bisulfate and 11 g purified water were added and a hydrolysis treatment was performed for 1 hour at 80° C. followed by the distillative removal of the low-boiling fraction under reduced pressure.

An additional 14 g purified water was added and a hydrolysis treatment was performed for 3 hours at 80° C., followed by distillative removal of the low-boiling fraction under reduced pressure proceeding as previously described. The obtained reaction product was cooled to room temperature and returned to ambient pressure and was mixed with 10 g diatomaceous earth and a solid/liquid separation process (removal of the catalyst) was performed by carrying out a pressure filtration. A "polyoxyalkylene-modified polysiloxane composition 2" was obtained as the filtrate provided by this process.

Practical Example 3

The following were introduced into a 1000-mL (1 L) four-neck flask equipped with a stirrer, reflux condenser, thermometer, and nitrogen inlet port: 409 g of a methylhydrogenpolysiloxane with the structural formula

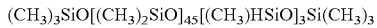

that exhibited a hydrogen gas production of 18.3 mL/g and 291 g of an allyl polyether with the structural formula $CH_2=CHCH_2O(C_2H_4O)_{12}CH_3$. To this was added a platinum/divinyltetramethyldisiloxane-toluene solution having a platinum concentration of 3.0 mass %, and a reaction was run for 2 hours at 80° C.

The low-boiling fraction was then distilled out under reduced pressure followed by the addition of 0.105 g potassium bisulfate and 11 g purified water. A hydrolysis treatment was performed for 2 hours at 80° C. followed by the distillative removal of the low-boiling fraction under reduced pressure and filtration at room temperature.

600 g of the resulting filtrate was transferred to an autoclave and 30 g of a Raney nickel catalyst was added, followed by the introduction of hydrogen and the execution of a hydrogenation reaction for 6 hours at a temperature of 140° C. and a pressure of 80 kg/cm$^2$. Using a 0.1 µm filtration filter, a solid/liquid separation process (removal of the catalyst) was then performed on the catalyst by carrying out a pressure filtration.

The low-boiling fraction was then distillatively removed from 500 g of this filtrate under reduced pressure to obtain a "polyoxyalkylene-modified polysiloxane composition 3".

Practical Example 4

The following were introduced into a 1000-mL (1 L) four-neck flask equipped with a stirrer, reflux condenser, thermometer, and nitrogen inlet port: 165 g of a methylhydrogenpolysiloxane with the structural formula

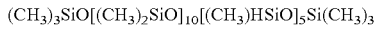

that exhibited a hydrogen gas production of 93.2 mL/g and 535 g of an allyl polyether with the structural formula $CH_2=CHCH_2O(C_2H_4O)_{12}CH_3$. To this was added a platinum/divinyltetramethyldisiloxane-toluene solution having a platinum concentration of 3.0 mass %, and a reaction was run for 2 hours at 80° C.

600 g of the resulting reaction solution was transferred to an autoclave and 30 g of a Raney nickel catalyst was added, followed by the introduction of hydrogen and the execution of a hydrogenation reaction for 6 hours at a temperature of 140° C. and a pressure of 80 kg/cm$^2$. Using a 0.1 µm filtration filter, a solid/liquid separation process (removal of the catalyst) was then performed on the catalyst by carrying out a pressure filtration.

To 500 g of this filtrate were added 0.04 g potassium bisulfate and 11 g purified water. A hydrolysis treatment was performed for 3 hours at 80° C. followed by the distillative removal of the low-boiling fraction under reduced pressure and filtration at room temperature to obtain a "polyoxyalkylene-modified polysiloxane composition 4".

Comparative Example 1

A "comparative sample 1" was obtained proceeding as in Example 1, but in this case carrying out the hydrolysis treatment for 3 hours at 80° C. after the addition of only 12 g purified water instead of the treatment with sodium bisulfate monohydrate of Example 1.

Comparative Example 2

A "comparative sample 2" was obtained proceeding as in Example 1, but in this case replacing the treatment with sodium bisulfate monohydrate of Example 1 with the addition of 7 g of a 0.1 mol/L aqueous hydrochloric acid solution, execution of a hydrolysis treatment for 3 hours at 80° C., and neutralization by the addition of 1.5 g of a 5% aqueous sodium bicarbonate solution.

Comparative Example 3

A "comparative sample 3" was obtained proceeding as in Example 2, but in this case replacing the ammonium bisulfate used in Example 2 with the addition of 0.04 g sodium acetate and carrying out the hydrolysis treatment for 2 hours at 90° C.

Comparative Example 4

A "comparative sample 4" was obtained proceeding as in Example 2, but in this case replacing the ammonium bisulfate used in Example 2 with the addition of 0.04 g sodium sulfate and carrying out the hydrolysis treatment for 2 hours at 90° C.

Comparative Example 5

A "comparative sample 5" was obtained proceeding as in Example 2, but in this case replacing the ammonium bisulfate used in Example 2 with the addition of 0.04 g sodium dihydrogen phosphate dihydrate and carrying out the hydrolysis treatment for 2 hours at 90° C. The pH of the aqueous solution provided by dissolving 50 g sodium dihydrogen phosphate dihydrate in 1 L water is approximately 4.3.

Comparative Example 6

Proceeding as in Example 2, 0.04 g zirconia sulfate "SZA-60" from Japan Energy Corporation was added in place of the ammonium bisulfate; a hydrolysis treatment was carried out for 2 hours at 90° C.; the low-boiling fraction was subsequently distilled off under reduced pressure; the obtained reaction product was cooled to room temperature and returned to ambient pressure; and 10 g diatomaceous earth was admixed and a solid/liquid separation process was run by carrying out a pressure filtration. The filtrate was designated as "comparative sample 6".

Comparative Example 7

Proceeding as in Example 2, 0.8 g zirconia sulfate "SZA-60" from Japan Energy Corporation was added in place of the ammonium bisulfate; a hydrolysis treatment was carried out for 2 hours at 90° C.; the low-boiling fraction was subsequently distilled off under reduced pressure; the obtained reaction product was cooled to room temperature and returned to ambient pressure; and 10 g diatomaceous earth was admixed and a solid/liquid separation process was run by carrying out a pressure filtration. The filtrate was designated as "comparative sample 7".

Comparative Example 8

The following were introduced into a 1000-mL (1 L) four-neck flask equipped with a stirrer, reflux condenser, thermometer, and nitrogen inlet port: 500 g of a methylhydrogenpolysiloxane with the structural formula

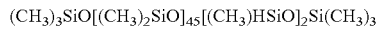
$(CH_3)_3SiO[(CH_3)_2SiO]_{45}[(CH_3)HSiO]_2Si(CH_3)_3$ that exhibited a hydrogen gas production of 12.2 mL/g; 200 g of an allyl polyether with the structural formula $CH_2$=$CHCH_2O(C_2H_4O)_{10}H$; and 200 g isopropyl alcohol (IPA). To this was added a platinum/divinyltetramethyldisiloxane-toluene solution having a platinum concentration of 3.0 mass %, and a reaction was run for 3 hours at 80° C.

600 g of this reaction solution was then transferred to an autoclave and 30 g of a Raney nickel catalyst was added, followed by the introduction of hydrogen and the execution of a hydrogenation reaction for 6 hours at a temperature of 140° C. and a pressure of 80 kg/cm$^2$. The obtained reaction product was thereafter cooled to room temperature and returned to ambient pressure; 10 g diatomaceous earth was admixed; and a solid/liquid separation process was then performed by carrying out a pressure filtration.

The low-boiling fraction was thereafter distillatively removed from 500 g of this filtrate under reduced pressure to obtain a "comparative sample 8".

Each of the compositions obtained in Examples 1 to 4 and Comparative Examples 1 to 8 was subjected to Odor Test 1 and Odor Test 2 and was evaluated for the presence/absence of cleavage of the silicon-oxygen bond in the organopolysiloxane moiety; the results are given in Table 1 below.

TABLE 2

Odor evaluation and presence/absence of silicon-oxygen bond cleavage for the samples in the examples and comparative examples

|  | nature of the deodorization treatment | Odor Test 1 (carbonyl value) | Odor Test 2 (odor) | presence/absence of silicon-oxygen bond cleavage |
|---|---|---|---|---|
| Practical Example 1 | hydrolysis (NaHSO$_4$) | 1.6 | +~++ | absent |
| Practical Example 2 | hydrolysis ((NH$_4$)HSO$_4$) | 1.5 | +~++ | absent |
| Practical Example 3 | hydrolysis (KHSO$_4$) + hydrogenation | 0.5 | ++ | absent |
| Practical Example 4 | hydrogenation + hydrolysis (KHSO$_4$) | 0.4 | ++ | absent |
| Comparative Example 1 | hydrolysis (only water) | 21.3 | x | absent |
| Comparative Example 2 | hydrolysis (aqueous hydrochloric acid solution) | 3.6 | + | present |
| Comparative Example 3 | hydrolysis (CH$_3$COONa) | 23.2 | x | present |
| Comparative Example 4 | hydrolysis (Na$_2$SO$_4$) | 22.0 | x | absent |
| Comparative Example 5 | hydrolysis (NaH$_2$PO$_4$) | 18.5 | x | absent |
| Comparative Example 6 | solid acid-mediated hydrolysis (small quantity of zirconia sulfate) | 12.6 | Δ | absent |
| Comparative Example 7 | solid acid-mediated hydrolysis (large quantity of zirconia sulfate) | 1.6 | + | present |
| Comparative Example 8 | hydrogenation | 3.2 | + | absent |

In the case of the polyoxyalkylene-modified polysiloxane compositions according to Examples 1 and 2 of the present application, there was almost no perception of unpleasant odor both immediately after production and with elapsed time.

Moreover, Examples 3 and 4 demonstrated that the combination with a hydrogenation procedure provided a substantially odor-free product even with elapsed time.

The occurrence of silicon-oxygen bond cleavage in the organopolysiloxane moiety was also found to be absent in all of Examples 1 to 4.

On the other hand, in the case of the comparative samples according to Comparative Examples 1 to 8, in which the odor-lowering treatment was not carried out using the special acidic inorganic salt according to the present invention, in all cases an evaluation was rendered of a stronger unpleasant odor than for the polyoxyalkylene-modified polysiloxane compositions according to the examples. In addition, in Comparative Example 7, in which a large amount of zirconia sulfate was used to achieve odor reduction, a certain odor reduction could be realized, but cleavage of the silicon-oxygen bond in the organopolysiloxane moiety was also occurred.

Practical Example 5

The following were introduced into a 1000-mL (1 L) four-neck flask equipped with a stirrer, reflux condenser, thermometer, and nitrogen inlet port: 500 g of a methylhydrogenpolysiloxane with the structural formula $(CH_3)_3SiO[(CH_3)_2SiO]_{45}[(CH_3)HSiO]_2Si(CH_3)_3$ that exhibited a hydrogen gas production of 12.2 mL/g; 200 g of an allyl polyether with the structural formula 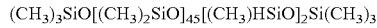$CH_2$=$CHCH_2O(C_2H_4O)_{10}H$; and 200 g isopropyl alcohol (IPA). To this was added a platinum/divinyltetramethyldisiloxane-toluene solution having a platinum concentration of 3.0 mass %, and a reaction was run for 3 hours at 80° C.

The low-boiling fraction was then distilled out under reduced pressure followed by the addition of 0.035 g sodium bisulfate monohydrate and 11 g purified water. A hydrolysis treatment was performed for 1 hour at 80° C. followed by the distillative removal of the low-boiling fraction under reduced pressure and filtration at room temperature with Filter Cel from Celite to yield a "polyoxyalkylene-modified polysiloxane composition 5". The obtained "polyoxyalkylene-modified organopolysiloxane composition 5" had a light transmittance (quartz cell, optical path length: 10 mm) at 480 nm of 99% and had an APHA color of not more than 10.

50 g of the obtained "polyoxyalkylene-modified polysiloxane composition 5" was also sampled into a 100-cc glass bottle and was heated for 5 hours at 100° C. After heating, this composition was not discolored and had maintained an APHA color of not more than 10.

Comparative Example 9

The following were introduced into a 1000-mL (1 L) four-neck flask equipped with a stirrer, reflux condenser, thermometer, and nitrogen inlet port: 500 g of a methylhydrogenpolysiloxane with the structural formula $(CH_3)_3SiO[(CH_3)_2SiO]_{45}[(CH_3)HSiO]_2Si(CH_3)_3$ that exhibited a hydrogen gas production of 12.2 mL/g; 200 g of an allyl polyether with the structural formula 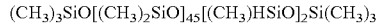$CH_2$=$CHCH_2O(C_2H_4O)_{10}H$; and 200 g isopropyl alcohol (IPA). To this was added a platinum/divinyltetramethyldisiloxane-toluene solution having a platinum concentration of 3.0 mass %, and a reaction was run for 3 hours at 80° C.

The low-boiling fraction was then distilled out under reduced pressure followed by the addition of 0.7 g zirconia sulfate "SZA-60" from Japan Energy Corporation and 11 g purified water. A hydrolysis treatment was performed for 1 hour at 80° C. followed by the distillative removal of the low-boiling fraction under reduced pressure. When filtration was performed with Filter Cel at room temperature, a slight white turbidity occurred, and the light transmittance (quartz cell, optical path length: 10 mm) at 480 nm was 90%. The obtained filtrate was re-filtered with Filter Cel to obtain a "comparative sample 9". The obtained "comparative sample 9" had a light transmittance (quartz cell, optical path length: 10 mm) at 480 nm of 99% and an APHA color of 10.

50 g of the obtained "comparative sample 9" was also sampled into a 100-cc glass bottle and was heated for 5 hours at 100° C. After heating, this sample was discolored and had become yellow. Its APHA color was 150.

Composition Example 1

Liquid Foundation

A liquid foundation is prepared from the following components. The numerical values are in mass % in all instances.

Oil Phase

| | |
|---|---|
| decamethylcyclopentasiloxane | 15.0 |
| liquid paraffin | 5.0 |
| para-methoxycinnamate ester | 3.0 |
| polyoxyalkylene-modified polysiloxane composition 5 (obtained in Example 5) | 2.0 |

Aqueous Phase

| | |
|---|---|
| purified water | 56.2 |
| glycerol | 5.0 |
| water-soluble preservative | suitable quantity |

Powder Component

| | |
|---|---|
| hydrophobed titanium oxide | 10.0 |
| talc | 3.8 |
| colored pigment | suitable quantity |

<Production Method>

The oil phase and aqueous phase are each heated to bring about dissolution. After the aqueous phase has been heated and dissolved, the powder component is thoroughly dispersed with stirring in the aqueous phase and heating to 75° C. is carried out. The thusly obtained aqueous phase is added with stirring to the oil phase; emulsification and dispersion are performed using a homomixer; and the product is obtained by cooling to room temperature.

<Evaluation>

The thusly obtained liquid foundation exhibits a light spreadability and has an excellent and refreshing usability and use sensation that are free of stickiness. In addition, this is a cosmetic that has an excellent timewise stability for which no change in smell is observed with elapsed time.

Composition Example 2

Sunscreen Cosmetic

A sunscreen cosmetic is prepared from the following components. The numerical values are in mass % in all instances.

Oil Phase

| | |
|---|---|
| decamethylcyclopentasiloxane | 25.0 |
| hydrophobed titanium oxide | 10.0 |
| hydrophobed talc | 4.0 |
| squalane | 5.0 |
| polyoxyalkylene-modified polysiloxane composition 1 (obtained in Example 1) | 2.0 |
| organomodified montmorillonite | 1.0 |
| preservative | suitable quantity |
| fragrance | suitable quantity |

Aqueous Phase

| | |
|---|---|
| purified water | 46.0 |
| dipropylene glycol | 7.0 |

<Production Method>

The oil phase and aqueous phase are each heated to 60° C. to bring about dissolution. The aqueous phase is added to the oil phase; emulsification into uniform particles is performed using a homomixer; and cooling was carried out to give the product.

<Evaluation>

The thusly obtained sunscreen cosmetic exhibits a light spreadability and has an excellent and refreshing usability and use sensation that are free of stickiness. In addition, this is a cosmetic that had an excellent timewise stability for which no change in smell is observed with elapsed time.

Composition Example 3

Treatment Gel

A treatment gel is prepared from the following components. The numerical values are in mass % in all instances.

Oil Phase

| | |
|---|---|
| ethanol | 20.0 |
| polyoxyalkylene-modified polysiloxane composition 2 (obtained in Example 2) | 2.0 |
| triisooctane glyceryl | 2.0 |
| Torayfil E-506S | 8.0 |

Aqueous Phase

| | |
|---|---|
| carboxyvinyl powder (1% aqueous solution) | 20.0 |
| triethanolamine | 0.2 |
| purified water | 49.3 |

<Production Method>

The oil phase and aqueous phase are each mixed to uniformity. The uniformly mixed oil phase is gradually added to the aqueous phase and the entire mass is brought to uniformity to provide the product.

<Evaluation>

The thusly obtained treatment gel exhibits a light spreadability and has an excellent and refreshing usability and use sensation that are free of stickiness. In addition, this is a cosmetic that has an excellent timewise stability for which no change in smell is observed with elapsed time.

The invention claimed is:

1. A production method of a polyoxyalkylene-modified polysiloxane composition, the production method comprising:
   a step [A] of synthesizing a polyoxyalkylene-modified polysiloxane composition by carrying out a hydrosilylation reaction between
   (a) a polyoxyalkylene compound that has a carbon-carbon double bond in molecular chain terminal position, and
   (b) an organohydrogenpolysiloxane; and
   a step [B] of removing an odor-causing substance by treating the polyoxyalkylene-modified polysiloxane composition in the presence of
   (c) at least one acidic inorganic salt that is a solid at 25° C., is soluble in water, and gives a pH at 25° C. of not more than 4 for the aqueous solution prepared by dissolving 50 g of component (c) in 1 liter of ion-exchanged water, wherein component (c) is at least one acidic inorganic salt comprising a hydrogensulfate ion $HSO_4^-$ and a monovalent cation M.

2. The production method according to claim 1, wherein component (c) is at least one acidic inorganic salt selected from the group consisting of sodium hydrogensulfate, potassium hydrogensulfate, and ammonium hydrogensulfate.

3. The production method according to claim 1 further comprising:
   a step [C] of carrying out a deodorization treatment by subjecting the polyoxyalkylene-modified polysiloxane composition to a hydrogenation reaction in the presence of a hydrogenation catalyst.

4. The production method according to claim 3, wherein step [C] is carried out subsequent to step [B].

5. The production method according to claim 3, wherein step [B] is carried out subsequent to step [C].

6. The production method according to claim 1, wherein component (a) in step [A] is a straight-chain polyoxyalkylene compound given by the following structural formula (1)

$$CH_2=CH-C_pH_{2p}O-(C_2H_4O)_{p1}(C_3H_6O)_{p2}R \quad (1)$$

wherein p is a number in the range from 1 to 10, p1 and p2 are numbers in the range from 0 to 30, (p1+p2) is a number in the range from 4 to 50, and R is the hydrogen atom or a $C_{1-10}$ alkyl group, and component (b) in step [A] is an organohydrogenpolysiloxane given by the following structural formula (2)

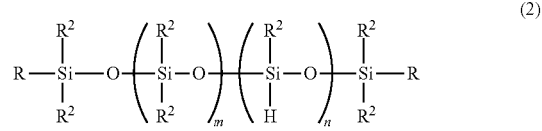

wherein $R^2$ is a substituted or unsubstituted monovalent hydrocarbyl group, R is the hydrogen atom or a group selected from $R^2$, m is a number in the range from 0 to 1000, and n is a number in the range from 0 to 200, wherein when n =0, at least one of R is the hydrogen atom.

7. The production method according to claim 1 further comprising, as a step preceding step [B] or a step following step [B], a stripping step of distillatively removing a low-boiling component from the polyoxyalkylene-modified polysiloxane composition under reduced pressure while in contact with nitrogen gas.

8. The production method according to claim 1, wherein component (a) in step [A] is a straight-chain polyoxyalkylene compound given by the following structural formula (1)

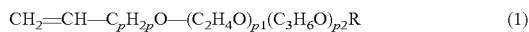  (1)

wherein p is a number in the range from 1 to 10, p1 and p2 are numbers in the range from 0 to 30, (p1+p2) is a number in the range from 4 to 50, and R is the hydrogen atom or a $C_{1-10}$ alkyl group, and component (b) in step [A] is an organohydrogenpolysiloxane given by the following structural formula (2)

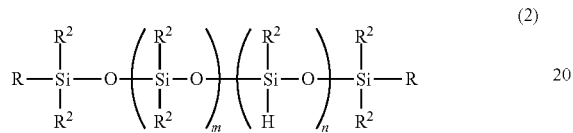  (2)

wherein $R^2$ is a substituted or unsubstituted monovalent hydrocarbyl group, R is the hydrogen atom or a group selected from $R^2$, m is a number in the range from 0 to 1000, and n is a number in the range from 0 to 200, wherein when n =0, at least one of R is the hydrogen atom.

* * * * *